(12) United States Patent
Li et al.

(10) Patent No.: US 9,371,296 B2
(45) Date of Patent: Jun. 21, 2016

(54) BICYCLIC 1,3,4-OXADIAZOLE DERIVATIVES AS SPHINGOSINE-1-PHOSPHATE RECEPTORS' MODULATORS

(71) Applicant: Allergan, Inc., Irvine, CA (US)

(72) Inventors: Ling Li, Irvine, CA (US); Janet A. Takeuchi, Irvine, CA (US); Ken Chow, Newport Coast, CA (US); Wha Bin Im, Irvine, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/937,542

(22) Filed: Nov. 10, 2015

(65) Prior Publication Data

US 2016/0137616 A1     May 19, 2016

Related U.S. Application Data

(60) Provisional application No. 62/080,711, filed on Nov. 17, 2014.

(51) Int. Cl.
*C07D 413/14* (2006.01)
*C07D 413/10* (2006.01)
*C07D 413/04* (2006.01)
*C07D 271/10* (2006.01)

(52) U.S. Cl.
CPC ............ *C07D 271/10* (2013.01); *C07D 413/04* (2013.01); *C07D 413/10* (2013.01); *C07D 413/14* (2013.01)

(58) Field of Classification Search
CPC .. C07D 271/10; C07D 413/14; C07D 413/10; C07D 413/04
See application file for complete search history.

(56) References Cited

FOREIGN PATENT DOCUMENTS

| JP | WO 2012054510 A1 * | 4/2012 | ............ C07D 413/12 |
| WO | 2015-073140 | 5/2015 | |
| WO | 2015-108577 | 7/2015 | |

OTHER PUBLICATIONS

Cross, L.C. et al, Rules for the Nomenclature of Organic Chemistry, Section E: Stereochemistry, Pure & Appl. Chem., 1976, 11-30, 45.
Handbook of Pharmaceutical Salts, P.Heinrich Stahl & Camille G. Wermuth (Eds), Verlag Helvetica Chemica Acta—Zürich, 2002, 329-345.

* cited by examiner

*Primary Examiner* — Matthew Coughlin
(74) *Attorney, Agent, or Firm* — Barbara C. Potts

(57) ABSTRACT

The present invention relates to bicyclic 1,3,4-oxadiazole derivatives, processes for preparing them, pharmaceutical compositions containing them and their use as pharmaceuticals as modulators of sphingosine-1-phosphate receptors.

19 Claims, No Drawings

BICYCLIC 1,3,4-OXADIAZOLE DERIVATIVES AS SPHINGOSINE-1-PHOSPHATE RECEPTORS' MODULATORS

CROSS-REFERENCE TO RELATED APPLICATIONS

This application claims the benefit of U.S. Provisional Application Ser. No. 62/080,711, filed on Nov. 17, 2014, which is incorporated herein by reference in its entirety.

FIELD OF THE INVENTION

The present invention relates to bicyclic 1,3,4-oxadiazole derivatives, processes for preparing them, pharmaceutical compositions containing them and their use as pharmaceuticals as modulators of sphingosine-1-phosphate receptors. The invention relates specifically to the use of these compounds and their pharmaceutical compositions to treat disorders associated with sphingosine-1-phosphate (S1P) receptor modulation, such as S1P1 modulation.

BACKGROUND OF THE INVENTION

Sphingosine-1-phosphate is stored in relatively high concentrations in human platelets, which lack the enzymes responsible for its catabolism, and it is released into the blood stream upon activation of physiological stimuli, such as growth factors, cytokines, receptor agonists and antigens. It may also play a critical role in platelet aggregation and thrombosis and could aggravate cardiovascular diseases. On the other hand, the relatively high concentration of the metabolite in high-density lipoproteins (HDL) may have beneficial implications for atherogenesis. For example, there are recent suggestions that sphingosine-1-phosphate, together with other lysolipids such as sphingosylphosphorylcholine and lysosulfatide, are responsible for the beneficial clinical effects of HDL by stimulating the production of the potent antiatherogenic signaling molecule nitric oxide by the vascular endothelium. In addition, like lysophosphatidic acid, it is a marker for certain types of cancer, and there is evidence that its role in cell division or proliferation may have an influence on the development of cancers. These are currently topics that are attracting great interest amongst medical researchers, and the potential for therapeutic intervention in sphingosine-1-phosphate metabolism is under active investigation.

SUMMARY OF THE INVENTION

We have now discovered a group of novel compounds which are potent and selective sphingosine-1-phosphate modulators. As such, the compounds described herein are useful in treating a wide variety of disorders associated with modulation of sphingosine-1-phosphate receptors. The term "modulator" as used herein, includes but is not limited to: receptor agonist, antagonist, inverse agonist, inverse antagonist, partial agonist, partial antagonist.

This invention describes compounds of Formula I and II, which have sphingosine-1-phosphate receptor biological activity. The compounds in accordance with the present invention are thus of use in medicine, for example, in the treatment of humans with diseases and conditions that are alleviated by S1P modulation, such as S1P1 modulation.

In one aspect, the invention provides a compound having Formula I:

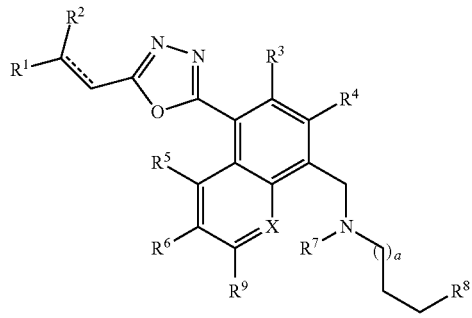

Formula I or an enantiomer or diastereoisomer thereof, or a tautomer or zwitterion of any one of the foregoing, or a pharmaceutically acceptable salt of any one of the foregoing;

wherein:

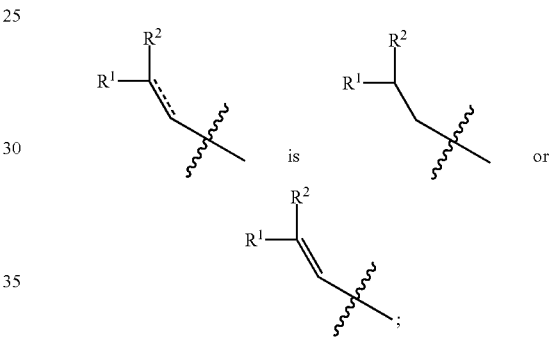

X is N or $CR^{12}$;

$R^1$ is substituted or unsubstituted aryl, substituted or unsubstituted heterocycle, substituted or unsubstituted $C_{5-8}$ cycloalkyl, or substituted or unsubstituted $C_{5-8}$ cycloalkenyl;

$R^2$ is substituted or unsubstituted $C_{1-8}$ alkyl;

$R^3$ is hydrogen, halogen, substituted or unsubstituted $C_{1-8}$ alkyl, $C(O)R^{13}$ or hydroxyl;

$R^4$ is hydrogen, halogen, substituted or unsubstituted $C_{1-8}$ alkyl, $C(O)R^{13}$ or hydroxyl;

$R^5$ is hydrogen, halogen, substituted or unsubstituted $C_{1-8}$ alkyl, $C(O)R^{13}$, hydroxyl, or substituted or unsubstituted heterocycle;

$R^6$ is hydrogen, halogen, substituted or unsubstituted $C_{1-8}$ alkyl, $C(O)R^{13}$, hydroxyl or substituted or unsubstituted heterocycle;

$R^7$ is H or substituted or unsubstituted $C_{1-8}$ alkyl;

$R^8$ is —$OPO_3H_2$, carboxylic acid, —$PO_3H_2$, —P(O)MeOH, —P(O)(H)OH or $OR^{10}$;

$R^9$ is hydrogen, halogen, substituted or unsubstituted $C_{1-8}$ alkyl, $C(O)R^{13}$, hydroxyl, or substituted or unsubstituted heterocycle;

$R^{10}$ is hydrogen or substituted or unsubstituted $C_{1-8}$ alkyl;

$R^{12}$ is hydrogen, halogen, substituted or unsubstituted $C_{1-8}$ alkyl, $C(O)R^{13}$ or hydroxyl;

$R^{13}$ is OH, substituted or unsubstituted $C_{1-8}$ alkyl or —$OC_{1-8}$ alkyl; and a is 0, 1, 2 or 3.

In another aspect, the invention provides a compound having Formula I, wherein:

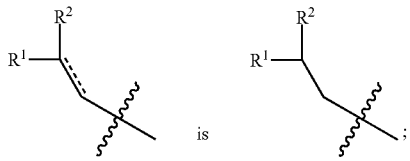

is

X is N or $CR^{12}$;
$R^1$ is substituted or unsubstituted aryl, substituted or unsubstituted heterocycle, substituted or unsubstituted $C_{5-8}$ cycloalkyl, or substituted or unsubstituted $C_{5-8}$ cycloalkenyl;
$R^2$ is substituted or unsubstituted $C_{1-8}$ alkyl;
$R^3$ is hydrogen, halogen, substituted or unsubstituted $C_{1-8}$ alkyl, $C(O)R^{13}$ or hydroxyl;
$R^4$ is hydrogen, halogen, substituted or unsubstituted $C_{1-8}$ alkyl, $C(O)R^{13}$ or hydroxyl;
$R^5$ is hydrogen, halogen, substituted or unsubstituted $C_{1-8}$ alkyl, $C(O)R^{13}$, hydroxyl, or substituted or unsubstituted heterocycle;
$R^6$ is hydrogen, halogen, substituted or unsubstituted $C_{1-8}$ alkyl, $C(O)R^{13}$, hydroxyl, or substituted or unsubstituted heterocycle;
$R^7$ is H or substituted or unsubstituted $C_{1-8}$ alkyl;
$R^8$ is —$OPO_3H_2$, carboxylic acid, —$PO_3H_2$, —P(O)MeOH, —P(O)(H)OH or $OR^{10}$;
$R^9$ is hydrogen, halogen, substituted or unsubstituted $C_{1-8}$ alkyl, $C(O)R^{13}$, hydroxyl, or substituted or unsubstituted heterocycle;
$R^{10}$ is hydrogen or substituted or unsubstituted $C_{1-8}$ alkyl;
$R^{12}$ is hydrogen, halogen, substituted or unsubstituted $C_{1-8}$ alkyl, $C(O)R^{13}$ or hydroxyl;
$R^{13}$ is OH, substituted or unsubstituted $C_{1-8}$ alkyl or —$OC_{1-8}$ alkyl; and
a is 0, 1, 2 or 3;
or an enantiomer or diastereoisomer thereof, or a tautomer or zwitterion of any one of the foregoing, or a pharmaceutically acceptable salt of any one of the foregoing.

In another aspect, the invention provides a compound having Formula I, wherein:

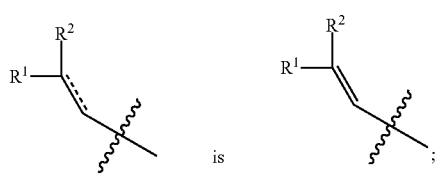

is

X is N or $CR^{12}$;
$R^1$ is substituted or unsubstituted aryl, substituted or unsubstituted heterocycle, substituted or unsubstituted $C_{5-8}$ cycloalkyl, or substituted or unsubstituted $C_{5-8}$ cycloalkenyl;
$R^2$ is substituted or unsubstituted $C_{1-8}$ alkyl;
$R^3$ is hydrogen, halogen, substituted or unsubstituted $C_{1-8}$ alkyl, $C(O)R^{13}$ or hydroxyl;
$R^4$ is hydrogen, halogen, substituted or unsubstituted $C_{1-8}$ alkyl, $C(O)R^{13}$ or hydroxyl;
$R^5$ is hydrogen, halogen, substituted or unsubstituted $C_{1-8}$ alkyl, $C(O)R^{13}$, hydroxyl, or substituted or unsubstituted heterocycle;
$R^6$ is hydrogen, halogen, substituted or unsubstituted $C_{1-8}$ alkyl, $C(O)R^{13}$, hydroxyl, or substituted or unsubstituted heterocycle;
$R^7$ is H or substituted or unsubstituted $C_{1-8}$ alkyl;
$R^8$ is —$OPO_3H_2$, carboxylic acid, —$PO_3H_2$, —P(O)MeOH, —P(O)(H)OH or $OR^{10}$;
$R^9$ is hydrogen, halogen, substituted or unsubstituted $C_{1-8}$ alkyl, $C(O)R^{13}$, hydroxyl, or substituted or unsubstituted heterocycle;
$R^{10}$ is hydrogen or substituted or unsubstituted $C_{1-8}$ alkyl;
$R^{12}$ is hydrogen, halogen, substituted or unsubstituted $C_{1-8}$ alkyl, $C(O)R^{13}$ or hydroxyl;
$R^{13}$ is OH, substituted or unsubstituted $C_{1-8}$ alkyl or —$OC_{1-8}$ alkyl; and
a is 0, 1, 2 or 3;
or an enantiomer or diastereoisomer thereof, or a tautomer or zwitterion of any one of the foregoing, or a pharmaceutically acceptable salt of any one of the foregoing.

In another aspect, the invention provides a compound having Formula I, wherein:

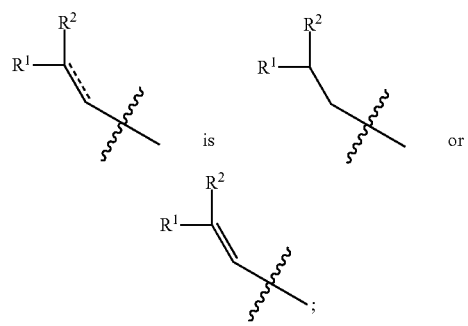

is or

;

X is N or $CR^{12}$;
$R^1$ is substituted or unsubstituted aryl, substituted or unsubstituted heterocycle, substituted or unsubstituted $C_{5-8}$ cycloalkyl, or substituted or unsubstituted $C_{5-8}$ cycloalkenyl;
$R^2$ is substituted or unsubstituted $C_{1-8}$ alkyl;
$R^3$ is hydrogen, halogen, substituted or unsubstituted $C_{1-8}$ alkyl, $C(O)R^{13}$ or hydroxyl;
$R^4$ is hydrogen, halogen, substituted or unsubstituted $C_{1-8}$ alkyl, $C(O)R^{13}$ or hydroxyl;
$R^5$ is hydrogen, halogen, substituted or unsubstituted $C_{1-8}$ alkyl, $C(O)R^{13}$, hydroxyl, or substituted or unsubstituted heterocycle;
$R^6$ is hydrogen, halogen, substituted or unsubstituted $C_{1-8}$ alkyl, $C(O)R^{13}$, hydroxyl or substituted or unsubstituted heterocycle;
$R^7$ is H or substituted or unsubstituted $C_{1-8}$ alkyl;
$R^8$ is —$OPO_3H_2$, carboxylic acid, —$PO_3H_2$, —P(O)MeOH, —P(O)(H)OH or $OR^{10}$;
$R^9$ is hydrogen, halogen, substituted or unsubstituted $C_{1-8}$ alkyl, $C(O)R^{13}$, hydroxyl or substituted or unsubstituted heterocycle;
$R^{10}$ is hydrogen or substituted or unsubstituted $C_{1-8}$ alkyl;
$R^{12}$ is hydrogen, halogen, substituted or unsubstituted $C_{1-8}$ alkyl, $C(O)R^{13}$ or hydroxyl;
$R^{13}$ is OH, substituted or unsubstituted $C_{1-8}$ alkyl or —$OC_{1-8}$ alkyl; and
a is 0, 1, 2 or 3;
or an enantiomer or diastereoisomer thereof, or a tautomer or zwitterion of any one of the foregoing, or a pharmaceutically acceptable salt of any one of the foregoing.

In another aspect, the invention provides a compound having Formula I, wherein a is 0 or 1.

In another aspect, the invention provides a compound having Formula I, wherein $R^8$ is carboxylic acid or $-PO_3H_2$. In another aspect, $R^8$ is $-PO_3H_2$.

In another aspect, the invention provides a compound having Formula I, wherein:

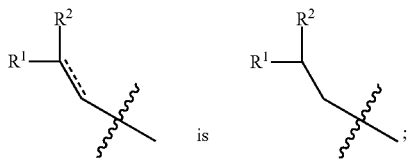

X is $CR^{12}$;
$R^1$ is substituted or unsubstituted aryl;
$R^2$ is substituted or unsubstituted $C_{1-8}$ alkyl;
$R^3$ is hydrogen;
$R^4$ is hydrogen;
$R^5$ is hydrogen;
$R^6$ is hydrogen;
$R^7$ is hydrogen;
$R^8$ is carboxylic acid or $-PO_3H_2$;
$R^9$ is hydrogen;
$R^{12}$ is hydrogen; and
a is 0, 1, 2 or 3;
or an enantiomer or diastereoisomer thereof, or a tautomer or zwitterion of any one of the foregoing, or a pharmaceutically acceptable salt of any one of the foregoing.

In another aspect, the invention provides a compound having Formula I, wherein:

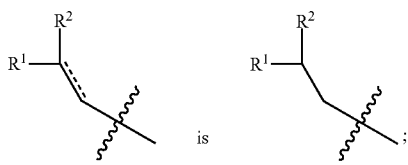

X is N;
$R^1$ is substituted or unsubstituted aryl;
$R^2$ is substituted or unsubstituted $C_{1-8}$ alkyl;
$R^3$ is hydrogen;
$R^4$ is hydrogen;
$R^5$ is hydrogen;
$R^6$ is hydrogen;
$R^7$ is hydrogen;
$R^8$ is carboxylic acid or $-PO_3H_2$;
$R^9$ is hydrogen; and
a is 0, 1, 2 or 3;
or an enantiomer or diastereoisomer thereof, or a tautomer or zwitterion of any one of the foregoing, or a pharmaceutically acceptable salt of any one of the foregoing.

In another aspect, the invention provides a compound having Formula I, wherein:

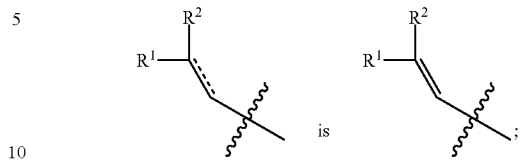

X is $CR^{12}$;
$R^1$ is substituted or unsubstituted aryl;
$R^2$ is substituted or unsubstituted $C_{1-8}$ alkyl;
$R^3$ is hydrogen;
$R^4$ is hydrogen;
$R^5$ is hydrogen;
$R^6$ is hydrogen;
$R^7$ is hydrogen;
$R^8$ is carboxylic acid or $-PO_3H_2$;
$R^9$ is hydrogen;
$R^{12}$ is hydrogen; and
a is 0, 1, 2 or 3;
or an enantiomer or diastereoisomer thereof, or a tautomer or zwitterion of any one of the foregoing, or a pharmaceutically acceptable salt of any one of the foregoing.

In another aspect, the invention provides a compound having Formula I, wherein:

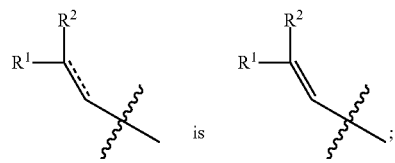

X is N;
$R^1$ is substituted or unsubstituted aryl;
$R^2$ is substituted or unsubstituted $C_{1-8}$ alkyl;
$R^3$ is hydrogen;
$R^4$ is hydrogen;
$R^5$ is hydrogen;
$R^6$ is hydrogen;
$R^7$ is hydrogen or substituted or unsubstituted $C_{1-8}$ alkyl;
$R^8$ is carboxylic acid or $-PO_3H_2$;
$R^9$ is hydrogen; and
a is 0, 1, 2 or 3;
or an enantiomer or diastereoisomer thereof, or a tautomer or zwitterion of any one of the foregoing, or a pharmaceutically acceptable salt of any one of the foregoing.

In another aspect, the invention provides a compound having Formula I, wherein:

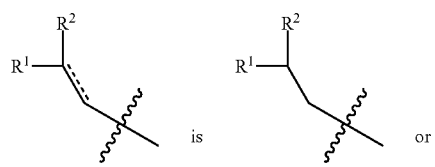

-continued

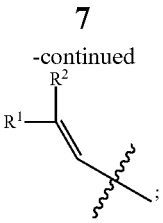

X is N or CR$^{12}$;
R$^1$ is unsubstituted aryl;
R$^2$ is unsubstituted C$_{1-6}$ alkyl;
R$^3$ is hydrogen;
R$^4$ is hydrogen;
R$^5$ is hydrogen;
R$^6$ is hydrogen;
R$^7$ is hydrogen;
R$^8$ is carboxylic acid or —PO$_3$H$_2$;
R$^9$ is hydrogen;
R$^{12}$ is hydrogen; and
a is 0 or 1;
or an enantiomer or diastereoisomer thereof, or a tautomer or zwitterion of any one of the foregoing, or a pharmaceutically acceptable salt of any one of the foregoing.

In another aspect, the invention provides a compound having Formula II:

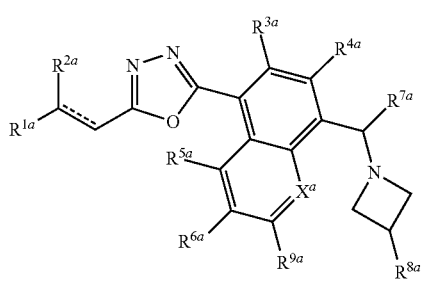

Formula II or an enantiomer or diastereoisomer thereof, or a tautomer or zwitterion of any one of the foregoing, or a pharmaceutically acceptable salt of any one of the foregoing; wherein:

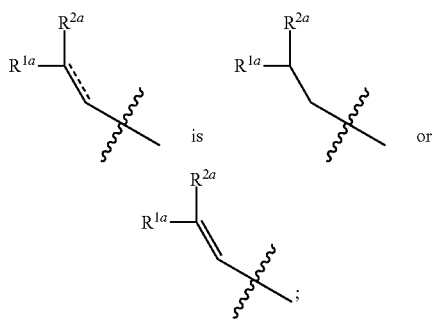

X$^a$ is N or CR$^{12a}$;
R$^{1a}$ is substituted or unsubstituted aryl, substituted or unsubstituted heterocycle, substituted or unsubstituted C$_{5-8}$ cycloalkyl, or substituted or unsubstituted C$_{5-8}$ cycloalkenyl;
R$^{2a}$ is substituted or unsubstituted C$_{1-8}$ alkyl;
R$^{3a}$ is hydrogen, halogen, substituted or unsubstituted C$_{1-8}$ alkyl, C(O)R$^{13a}$ or hydroxyl;
R$^{4a}$ is hydrogen, halogen, substituted or unsubstituted C$_{1-8}$ alkyl, C(O)R$^{13a}$ or hydroxyl;
R$^{5a}$ is hydrogen, halogen, substituted or unsubstituted C$_{1-8}$ alkyl, C(O)R$^{13a}$, hydroxyl, or substituted or unsubstituted heterocycle;
R$^{6a}$ is hydrogen, halogen, substituted or unsubstituted C$_{1-8}$ alkyl, C(O)R$^{13a}$, hydroxyl or substituted or unsubstituted heterocycle;
R$^{7a}$ is hydrogen or substituted or unsubstituted C$_{1-8}$ alkyl;
R$^{8a}$ is —OPO$_3$H$_2$, carboxylic acid, —PO$_3$H$_2$, —P(O)MeOH, —P(O)(H)OH or OR$^{10a}$;
R$^{9a}$ is hydrogen, halogen, substituted or unsubstituted C$_{1-8}$ alkyl, C(O)R$^{13a}$, hydroxyl or substituted or unsubstituted heterocycle;
R$^{10a}$ is hydrogen or substituted or unsubstituted C$_{1-8}$ alkyl;
R$^{12a}$ is hydrogen, halogen, substituted or unsubstituted C$_{1-8}$ alkyl, C(O)R$^{13a}$ or hydroxyl; and
R$^{13a}$ is OH, substituted or unsubstituted C$_{1-8}$ alkyl or —OC$_{1-8}$ alkyl.

In another aspect, the invention provides a compound having Formula II, wherein:

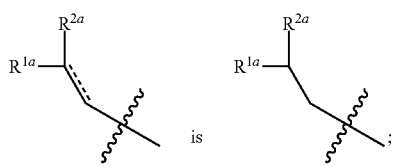

X$^a$ is N or CR$^{12a}$;
R$^a$ is substituted or unsubstituted aryl, substituted or unsubstituted heterocycle, substituted or unsubstituted C$_{5-8}$ cycloalkyl, or substituted or unsubstituted C$_{5-8}$ cycloalkenyl;
R$^{2a}$ is substituted or unsubstituted C$_{1-8}$ alkyl;
R$^{3a}$ is hydrogen, halogen, substituted or unsubstituted C$_{1-8}$ alkyl, C(O)R$^{13a}$ or hydroxyl;
R$^{4a}$ is hydrogen, halogen, substituted or unsubstituted C$_{1-8}$ alkyl, C(O)R$^{13a}$ or hydroxyl;
R$^{5a}$ is hydrogen, halogen, substituted or unsubstituted C$_{1-8}$ alkyl, C(O)R$^{13a}$, hydroxyl or substituted or unsubstituted heterocycle;
R$^{6a}$ is hydrogen, halogen, substituted or unsubstituted C$_{1-8}$ alkyl, C(O)R$^{13a}$, hydroxyl or substituted or unsubstituted heterocycle;
R$^{7a}$ is hydrogen or substituted or unsubstituted C$_{1-8}$ alkyl;
R$^{8a}$ is —OPO$_3$H$_2$, carboxylic acid, —PO$_3$H$_2$, —P(O)MeOH, —P(O)(H)OH or OR$^{10a}$;
R$^{9a}$ is hydrogen, halogen, substituted or unsubstituted C$_{1-8}$ alkyl, C(O)R$^{13a}$, hydroxyl or substituted or unsubstituted heterocycle;
R$^{10a}$ is hydrogen or substituted or unsubstituted C$_{1-8}$ alkyl;
R$^{12a}$ is hydrogen, halogen, substituted or unsubstituted C$_{1-8}$ alkyl, C(O)R$^{13a}$ or hydroxyl; and
R$^{13a}$ is OH, substituted or unsubstituted C$_{1-8}$ alkyl or —OC$_{1-8}$ alkyl;
or an enantiomer or diastereoisomer thereof, or a tautomer or zwitterion of any one of the foregoing, or a pharmaceutically acceptable salt of any one of the foregoing.

In another aspect, the invention provides a compound having Formula II, wherein:

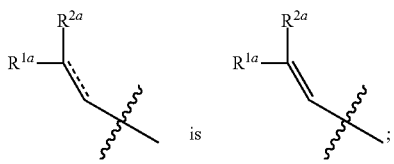

is ;

$X^a$ is N or $CR^{12a}$;
$R^{1a}$ is substituted or unsubstituted aryl, substituted or unsubstituted heterocycle, substituted or unsubstituted $C_{5-8}$ cycloalkyl, or substituted or unsubstituted $C_{5-8}$ cycloalkenyl;
$R^{2a}$ is substituted or unsubstituted $C_{1-8}$ alkyl;
$R^{3a}$ is hydrogen, halogen, substituted or unsubstituted $C_{1-8}$ alkyl, $C(O)R^{13a}$ or hydroxyl;
$R^{4a}$ is hydrogen, halogen, substituted or unsubstituted $C_{1-8}$ alkyl, $C(O)R^{13a}$ or hydroxyl;
$R^{5a}$ is hydrogen, halogen, substituted or unsubstituted $C_{1-8}$ alkyl, $C(O)R^{13a}$, hydroxyl or substituted or unsubstituted heterocycle;
$R^{6a}$ is hydrogen, halogen, substituted or unsubstituted $C_{1-8}$ alkyl, $C(O)R^{13a}$, hydroxyl or substituted or unsubstituted heterocycle;
$R^{7a}$ is hydrogen or substituted or unsubstituted $C_{1-8}$ alkyl;
$R^{8a}$ is —$OPO_3H_2$, carboxylic acid, —$PO_3H_2$, —$P(O)MeOH$, —$P(O)(H)OH$ or $OR^{10a}$;
$R^{9a}$ is hydrogen, halogen, substituted or unsubstituted $C_{1-8}$ alkyl, $C(O)R^{13a}$, hydroxyl or substituted or unsubstituted heterocycle;
$R^{10a}$ is hydrogen or substituted or unsubstituted $C_{1-8}$ alkyl;
$R^{12a}$ is hydrogen, halogen, substituted or unsubstituted $C_{1-8}$ alkyl, $C(O)R^{13a}$ or hydroxyl; and
$R^{13a}$ is OH, substituted or unsubstituted $C_{1-8}$ alkyl or —$OC_{1-8}$ alkyl;
or an enantiomer or diastereoisomer thereof, or a tautomer or zwitterion of any one of the foregoing, or a pharmaceutically acceptable salt of any one of the foregoing.

In another aspect, the invention provides a compound having Formula II, wherein:

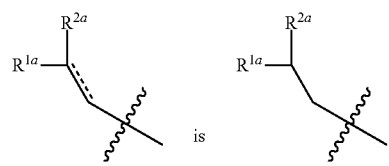

is ;

$X^a$ is N;
$R^{1a}$ is substituted or unsubstituted aryl;
$R^{2a}$ is substituted or unsubstituted $C_{1-8}$ alkyl;
$R^{3a}$ is hydrogen;
$R^{4a}$ is hydrogen;
$R^{5a}$ is hydrogen;
$R^{6a}$ is hydrogen;
$R^{7a}$ is hydrogen;
$R^{8a}$ is carboxylic acid; and
$R^{9a}$ is hydrogen;
or an enantiomer or diastereoisomer thereof, or a tautomer or zwitterion of any one of the foregoing, or a pharmaceutically acceptable salt of any one of the foregoing.

In another aspect, the invention provides a compound having Formula II, wherein:

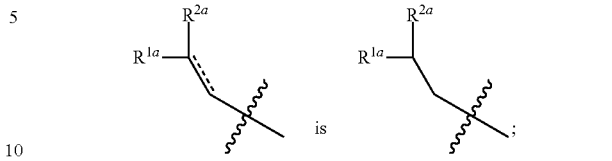

is ;

$X^a$ is $CR^{12a}$;
$R^{1a}$ is substituted or unsubstituted aryl;
$R^{2a}$ is substituted or unsubstituted $C_{1-8}$ alkyl;
$R^{3a}$ is hydrogen;
$R^{4a}$ is hydrogen;
$R^{5a}$ is hydrogen;
$R^{6a}$ is hydrogen;
$R^{7a}$ is hydrogen;
$R^{8a}$ is carboxylic acid;
$R^{9a}$ is hydrogen; and
$R^{12a}$ is hydrogen;
or an enantiomer or diastereoisomer thereof, or a tautomer or zwitterion of any one of the foregoing, or a pharmaceutically acceptable salt of any one of the foregoing.

In another aspect, the invention provides a compound having Formula II, wherein:

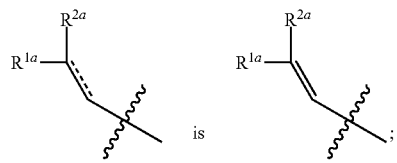

is ;

$X^a$ is N;
$R^{1a}$ is substituted or unsubstituted aryl;
$R^{2a}$ is substituted or unsubstituted $C_{1-8}$ alkyl;
$R^{3a}$ is hydrogen;
$R^{4a}$ is hydrogen;
$R^{5a}$ is hydrogen;
$R^{6a}$ is hydrogen;
$R^{7a}$ is hydrogen;
$R^{8a}$ is carboxylic acid; and
$R^{9a}$ is hydrogen;
or an enantiomer or diastereoisomer thereof, or a tautomer or zwitterion of any one of the foregoing, or a pharmaceutically acceptable salt of any one of the foregoing.

In another aspect, the invention provides a compound having Formula II, wherein:

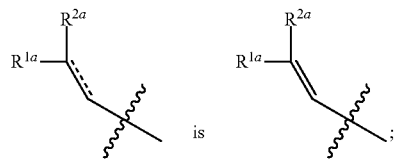

is ;

$X^a$ is $CR^{12a}$;
$R^{1a}$ is substituted or unsubstituted aryl;
$R^{2a}$ is substituted or unsubstituted $C_{1-8}$ alkyl;
$R^{3a}$ is hydrogen;
$R^{4a}$ is hydrogen;
$R^{5a}$ is hydrogen;

$R^{6a}$ is hydrogen;
$R^{7a}$ is hydrogen;
$R^{8a}$ is carboxylic acid;
$R^{9a}$ is hydrogen; and
$R^{12a}$ is hydrogen;
or an enantiomer or diastereoisomer thereof, or a tautomer or zwitterion of any one of the foregoing, or a pharmaceutically acceptable salt of any one of the foregoing.

In another aspect, the invention provides a compound having Formula II, wherein:

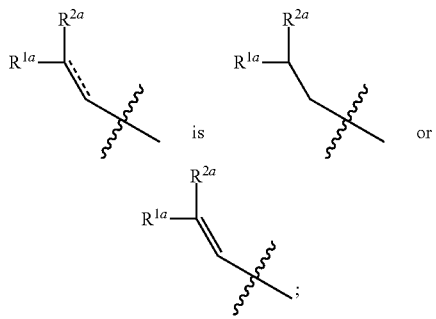

$X^a$ is N or $CR^{12a}$;
$R^{1a}$ is unsubstituted aryl;
$R^{2a}$ is unsubstituted $C_{1-6}$ alkyl;
$R^{3a}$ is hydrogen;
$R^{4a}$ is hydrogen;
$R^{5a}$ is hydrogen;
$R^{6a}$ is hydrogen;
$R^{7a}$ is hydrogen;
$R^{8a}$ is carboxylic acid;
$R^{9a}$ is hydrogen; and
$R^{12a}$ is hydrogen;
or an enantiomer or diastereoisomer thereof, or a tautomer or zwitterion of any one of the foregoing, or a pharmaceutically acceptable salt of any one of the foregoing.

In another aspect, the invention provides a compound having Formula II, wherein $R^8$ is carboxylic acid or —$PO_3H_2$. In another aspect, $R^8$ is carboxylic acid. In yet another aspect, $R^8$ is —$PO_3H_2$.

The term "alkyl", as used herein, refers to saturated, monovalent or divalent hydrocarbon moieties having linear or branched moieties or combinations thereof and containing 1 to 8 carbon atoms, such as methyl, ethyl, propyl, iso-propyl, butyl, iso-butyl, sec-butyl, tert-butyl, pentyl, iso-pentyl, neo-pentyl, hexyl, 2-methylpentyl, 3-methylpentyl, 2,2-dimethylbutyl, 2,3-dimethylbutyl. One methylene (—$CH_2$—) group of the alkyl can be replaced by oxygen, sulfur, sulfoxide, carbonyl, carboxyl, sulfonyl, or by a divalent $C_{3-6}$ cycloalkyl; one methane (CH) group of the alkyl can be replaced by nitrogen. Alkyl groups can be independently substituted with one or more halogen, hydroxyl, $C_{3-6}$ cycloalkyl, amino, non-aromatic heterocycle, carboxylic acid, phosphonic acid, sulphonic acid and/or phosphoric acid groups.

The term "cycloalkyl", as used herein, refers to a monovalent or divalent group of 3 to 8 carbon atoms derived from a saturated cyclic hydrocarbon. Cycloalkyl groups can be monocyclic or polycyclic. Cycloalkyl can be independently substituted with one or more $C_{1-8}$ alkyl groups or halogens.

The term "cycloalkenyl", as used herein, refers to a monovalent or divalent group of 5 to 8 carbon atoms derived from a saturated cycloalkyl having one double bond. Cycloalkenyl groups can be monocyclic or polycyclic. Cycloalkenyl groups can be independently substituted with one or more $C_{1-8}$ alkyl groups or halogens.

The term "halogen", as used herein, refers to an atom of chlorine, bromine, fluorine, iodine.

The term "heterocycle" as used herein, refers to a 3 to 10 membered ring, which can be aromatic or non-aromatic, saturated or non-saturated, monocyclic or polycyclic, containing at least one heteroatom selected form O, N and S, and combinations of at least two thereof, interrupting the carbocyclic ring structure. The heterocyclic ring can be interrupted by a C=O; the S or N heteroatom can be oxidized. Heterocyclic ring moieties can be independently substituted with one or more hydroxyl, $C_{1-8}$ alkyl or halogens.

The term "aryl" as used herein, refers to an organic moiety derived from an aromatic hydrocarbon consisting of a ring containing 6 to 10 carbon atoms by removal of one hydrogen. Aryl groups can be independently substituted with halogen atoms or $C_{1-8}$alkyl groups.

The term "hydroxyl" as used herein, represents a group of formula "—OH".

The term "carbonyl" as used herein, represents a group of formula "—C(O)".

The term "carboxyl" as used herein, represents a group of formula "—C(O)O—".

The term "sulfonyl" as used herein, represents a group of formula "—$SO_2$".

The term "sulfate" as used herein, represents a group of formula "—O—S(O)$_2$—O—".

The term "carboxylic acid" as used herein, represents a group of formula "—C(O)OH".

The term "sulfoxide" as used herein, represents a group of formula "—S=O".

The term "phosphonic acid" as used herein, represents a group of formula "—P(O)(OH)$_2$".

The term "phosphoric acid" as used herein, represents a group of formula "—(O)P(O)(OH)$_2$".

The term "sulphonic acid" as used herein, represents a group of formula "—S(O)$_2$OH".

Some compounds of the invention are:

(3-{[(4-{5-[(1E)-2-phenylpent-1-en-1-yl]-1,3,4-oxadiazol-2-yl}naphthalen-1-yl)methyl]amino}propyl)phosphonic acid
3-{[(4-{5-[(1E)-2-phenylpent-1-en-1-yl]-1,3,4-oxadiazol-2-yl}naphthalen-1-yl)methyl]amino}propanoic acid
(3-{[(4-{5-[(1E)-2-phenylhex-1-en-1-yl]-1,3,4-oxadiazol-2-yl}naphthalen-1-yl)methyl]amino}propyl) phosphonic acid
3-{[(4-{5-[(1E)-2-phenylhex-1-en-1-yl]-1,3,4-oxadiazol-2-yl}naphthalen-1-yl)methyl]amino}propanoic acid
(3-{[(5-{5-[(1E)-2-phenylpent-1-en-1-yl]-1,3,4-oxadiazol-2-yl}quinolin-8-yl)methyl]amino}propyl) phosphonic acid
3-{[(5-{5-[(1E)-2-phenylpent-1-en-1-yl]-1,3,4-oxadiazol-2-yl}quinolin-8-yl)methyl]amino}propanoic acid
(3-{[(5-{5-[(1E)-2-phenylhex-1-en-1-yl]-1,3,4-oxadiazol-2-yl}quinolin-8-yl)methyl]amino}propyl) phosphonic acid
3-{[(5-{5-[(1E)-2-phenylhex-1-en-1-yl]-1,3,4-oxadiazol-2-yl}quinolin-8-yl)methyl]amino}propanoic acid
{3-[({4-[5-(2-phenylheptyl)-1,3,4-oxadiazol-2-yl]naphthalen-1-yl}methyl)amino]propyl}phosphonic acid
3-[({4-[5-(2-phenylheptyl)-1,3,4-oxadiazol-2-yl]naphthalen-1-yl}methyl)amino]propanoic acid
{3-[({5-[5-(2-phenylpentyl)-1,3,4-oxadiazol-2-yl]quinolin-8-yl}methyl)amino]propyl}phosphonic acid
3-[({5-[5-(2-phenylpentyl)-1,3,4-oxadiazol-2-yl]quinolin-8-yl}methyl)amino]propanoic acid
1-[(4-{5-[(1E)-2-phenylpent-1-en-1-yl]-1,3,4-oxadiazol-2-yl}naphthalen-1-yl)methyl]azetidine-3-carboxylic acid
1-[(4-{5-[(1E)-2-phenylhex-1-en-1-yl]-1,3,4-oxadiazol-2-yl}naphthalen-1-yl)methyl]azetidine-3-carboxylic acid
(E)-1-((5-(5-(2-phenylpent-1-en-1-yl)-1,3,4-oxadiazol-2-yl)quinolin-8-yl)methyl)azetidine-3-carboxylic acid -continued 1-[(5-{5-[(1E)-2-phenylhex-1-en-1-yl]-1,3,4-oxadiazol-2-yl}quinolin-8-yl)methyl]azetidine-3-carboxylic acid
1-({4-[5-(2-phenylheptyl)-1,3,4-oxadiazol-2-yl]naphthalen-1-yl}methyl)azetidine-3-carboxylic acid
1-({5-[5-(2-phenylpentyl)-1,3,4-oxadiazol-2-yl]quinolin-8-yl}methyl)azetidine-3-carboxylic acid
3-[({5-[5-(2-phenylhexyl)-1,3,4-oxadiazol-2-yl]quinolin-8-yl}methyl)amino]propanoic acid
3-[({5-[5-(2-phenylheptyl)-1,3,4-oxadiazol-2-yl]quinolin-8-yl}methyl)amino]propanoic acid
{3-[({5-[5-(2-phenylhexyl)-1,3,4-oxadiazol-2-yl]quinolin-8-yl}methyl)amino]propyl}phosphonic acid
{3-[({5-[5-(2-phenylheptyl)-1,3,4-oxadiazol-2-yl]quinolin-8-yl}methyl)amino]propyl}phosphonic acid
1-({5-[5-(2-phenylhexyl)-1,3,4-oxadiazol-2-yl]quinolin-8-yl}methyl)azetidine-3-carboxylic acid
1-({5-[5-(2-phenylheptyl)-1,3,4-oxadiazol-2-yl]quinolin-8-yl}methyl)azetidine-3-carboxylic acid and pharmaceutically acceptable salts thereof.

Some compounds of the invention of Formula I are:

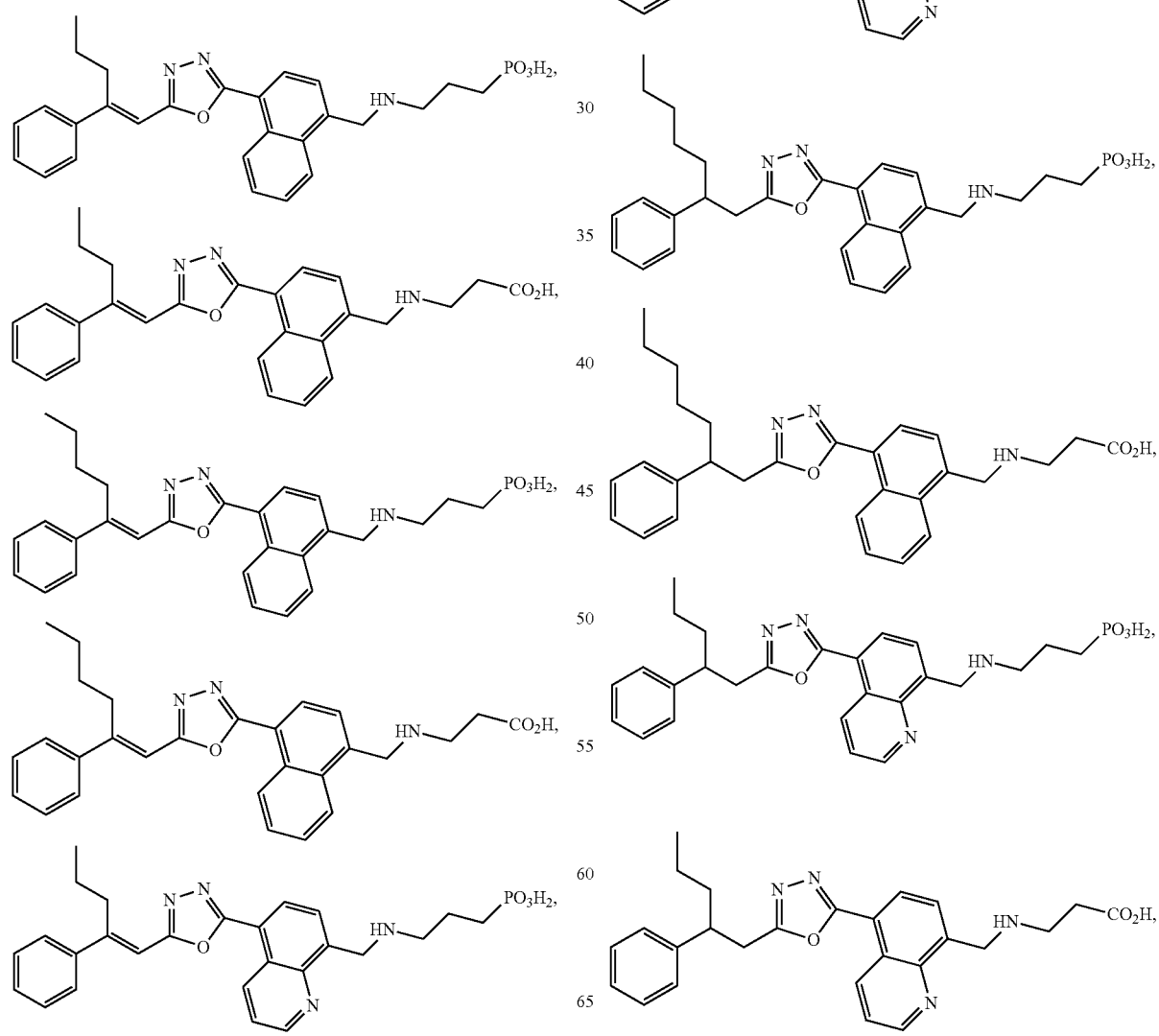

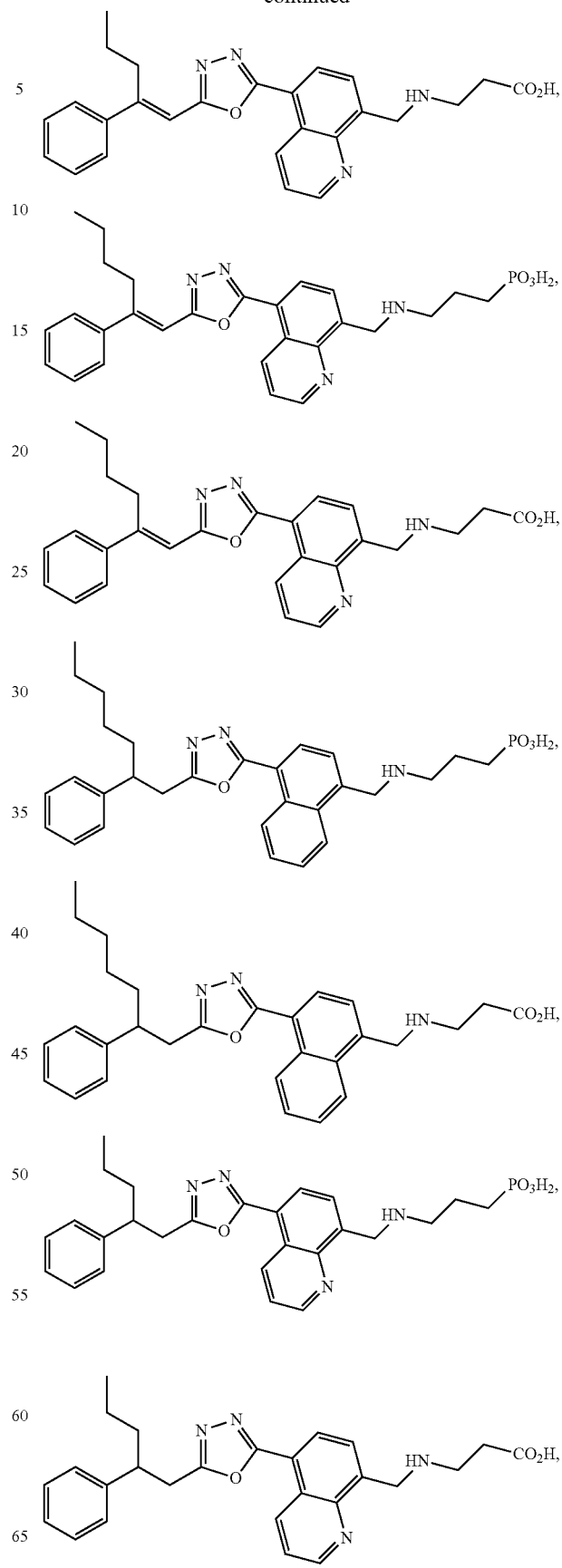

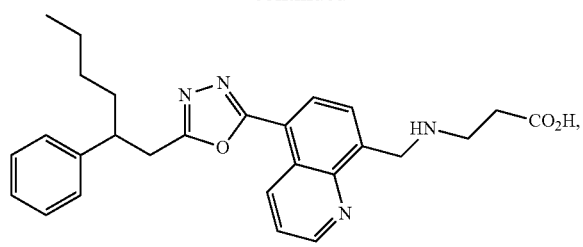
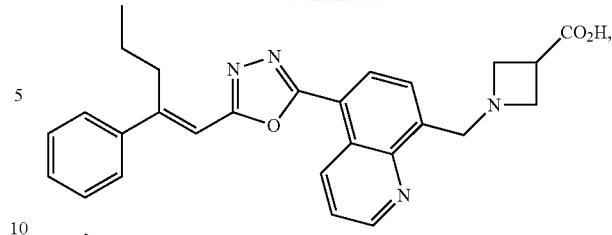
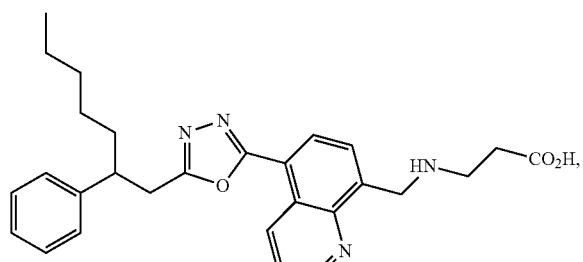
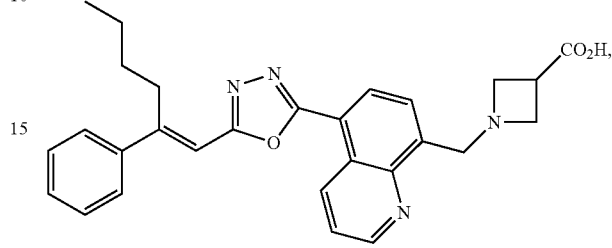
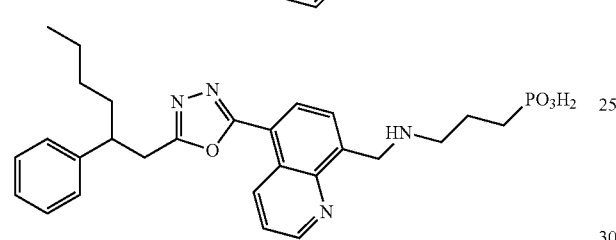
and
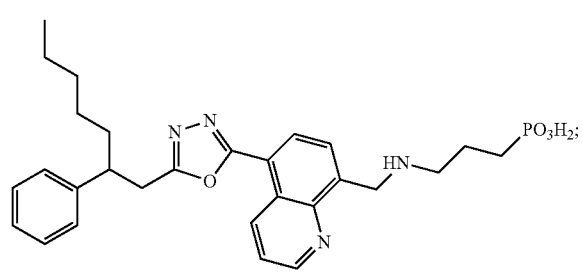
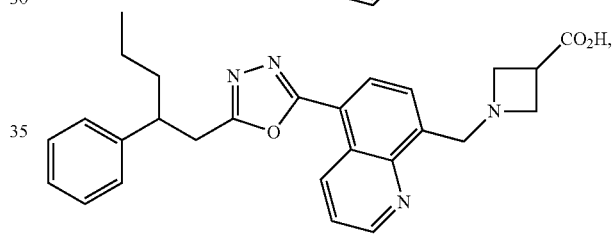
and pharmaceutically acceptable salts thereof.
Some compounds of the invention of Formula II are:
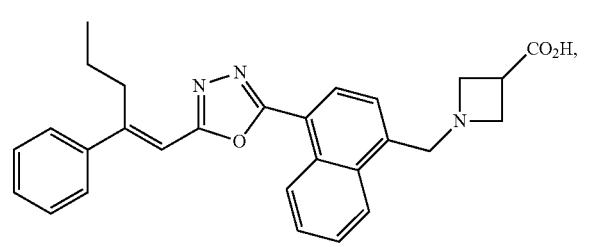
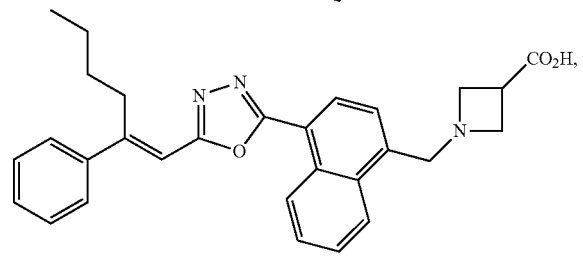
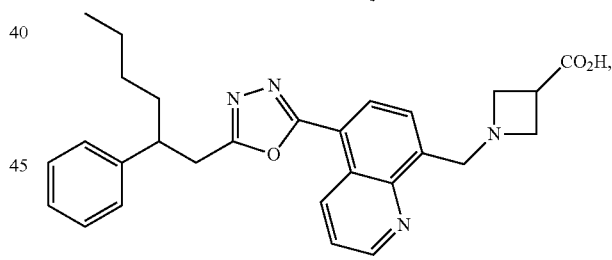
and pharmaceutically acceptable salts thereof.
Some compounds of Formula I or II and some of their intermediates have at least one stereocenter in their structure. This stereocenter may be present in an R or S configuration, said R and S notation is used in correspondence with the rules described in Pure Appl. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I or II are able to form.

The acid addition salt form of a compound of Formula I or II that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric acid, methylsulfonic acid, ethanesulfonic acid, benzenesulfonic acid, formic and the like (Handbook of Pharmaceutical Salts, P. Heinrich Stahl & Camille G. Wermuth (Eds), Verlag Helvetica Chimica Acta, Zürich, 2002, 329-345).

The base addition salt form of a compound of Formula I or II that occurs in its acid form can be obtained by treating the acid with an appropriate base such as an inorganic base, for example, sodium hydroxide, magnesium hydroxide, potassium hydroxide, calcium hydroxide, ammonia and the like; or an organic base such as for example, L-Arginine, ethanolamine, betaine, benzathine, morpholine and the like (Handbook of Pharmaceutical Salts, P. Heinrich Stahl & Camille G. Wermuth (Eds), Verlag Helvetica Chimica Acta, Zurich, 2002, 329-345).

Compounds of Formula I or II and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the sphingosine-1-phosphate receptors.

In another embodiment, there are provided pharmaceutical compositions including at least one compound of the invention in a pharmaceutically acceptable carrier.

In a further embodiment of the invention, there are provided methods for treating disorders associated with modulation of sphingosine-1-phosphate receptors. Such methods can be performed, for example, by administering to a subject in need thereof a pharmaceutical composition containing a therapeutically effective amount of at least one compound of the invention.

These compounds are useful for the treatment of mammals, including humans, with a range of conditions and diseases that are alleviated by S1P modulation.

Therapeutic utilities of S1P modulators include diseases, such as but not limited to:

Ocular Diseases: ocular angiogenesis, wet macular degeneration, dry macular degeneration, age-related macular degeneration, diabetic retinopathy, retinopathy of prematurity, retinal edema, dry eye, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis;

Systemic vascular barrier related diseases: various inflammatory diseases, including acute lung injury, its prevention, sepsis, tumor metastasis, atherosclerosis, pulmonary edemas, and ventilation-induced lung injury;

Autoimmune diseases and immunosuppression: rheumatoid arthritis, Crohn's disease, Graves' disease, systemic lupus erythematosus, inflammatory bowel disease, multiple sclerosis, Myasthenia gravis, psoriasis, ulcerative colitis, autoimmune uveitis, renal ischemia/perfusion injury, contact hypersensitivity, atopic dermatitis, and organ transplantation;

Allergies and other inflammatory diseases: urticaria, bronchial asthma, and other airway inflammations including pulmonary emphysema and chronic obstructive pulmonary diseases;

Cardiac functions: bradycardia, congestive heart failure, cardiac arrhythmia, prevention and treatment of atherosclerosis, and ischemia/reperfusion injury;

Wound Healing: scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries;

Bone formation: treatment of osteoporosis and various bone fractures including hip and ankles;

Anti-nociceptive activity: visceral pain, pain associated with diabetic neuropathy, rheumatoid arthritis, chronic knee and joint pain, tendonitis, osteoarthritis, neuropathic pains;

Anti-fibrosis: ocular, cardiac, hepatic and pulmonary fibrosis, proliferative vitreoretinopathy, cicatricial pemphigoid, surgically induced fibrosis in cornea, conjunctiva and tenon;

Pains and anti-inflammation: acute pain, flare-up of chronic pain, musculo-skeletal pains, visceral pain, pain associated with diabetic neuropathy, rheumatoid arthritis, chronic knee and joint pain, tendonitis, osteoarthritis, bursitis, neuropathic pain;

CNS neuronal injuries: Alzheimer's disease, age-related neuronal injuries;

Organ transplants: renal, corneal, cardiac and adipose tissue transplants.

In still another embodiment of the invention, there are provided methods for treating disorders associated with modulation of sphingosine-1-phosphate receptors. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The present invention concerns the use of a compound of Formula I or II, or a pharmaceutically acceptable salt thereof, for the manufacture of a medicament for the treatment of:

Ocular Diseases: ocular angiogenesis, wet macular degeneration, dry macular degeneration, age-related macular degeneration, diabetic retinopathy, retinopathy of prematurity, retinal edema, dry eye, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis;

Systemic vascular barrier related diseases: various inflammatory diseases, including acute lung injury, its prevention, sepsis, tumor metastasis, atherosclerosis, pulmonary edemas, and ventilation-induced lung injury;

Autoimmune diseases and immunosuppression: rheumatoid arthritis, Crohn's disease, Graves' disease, systemic lupus erythematosus, inflammatory bowel disease, multiple sclerosis, Myasthenia gravis, psoriasis, ulcerative colitis, antoimmune uveitis, renal ischemia/perfusion injury, contact hypersensitivity, atopic dermatitis, and organ transplantation;

Allergies and other inflammatory diseases: urticaria, bronchial asthma, and other airway inflammations including pulmonary emphysema and chronic obstructive pulmonary diseases;

Cardiac functions: bradycardia, congestive heart failure, cardiac arrhythmia, prevention and treatment of atherosclerosis, and ischemia/reperfusion injury;

Wound Healing: scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries;

Bone formation: treatment of osteoporosis and various bone fractures including hip and ankles;

Anti-nociceptive activity: visceral pain, pain associated with diabetic neuropathy, rheumatoid arthritis, chronic knee and joint pain, tendonitis, osteoarthritis, neuropathic pains;

Anti-fibrosis: ocular, cardiac, hepatic and pulmonary fibrosis, proliferative vitreoretinopathy, cicatricial pemphigoid, surgically induced fibrosis in cornea, conjunctiva and tenon;

Pains and anti-inflammation: acute pain, flare-up of chronic pain, musculo-skeletal pains, visceral pain, pain associated with diabetic neuropathy, rheumatoid arthritis, chronic knee and joint pain, tendonitis, osteoarthritis, bursitis, neuropathic pains;

CNS neuronal injuries: Alzheimer's disease, age-related neuronal injuries;

Organ transplants: renal, corneal, cardiac and adipose tissue transplants.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Pharmaceutical compositions containing invention compounds may be in a form suitable for topical use, for example, as oily suspensions, as solutions or suspensions in aqueous liquids or nonaqueous liquids, or as oil-in-water or water-in-oil liquid emulsions. Pharmaceutical compositions may be prepared by combining a therapeutically effective amount of at least one compound according to the present invention, or a pharmaceutically acceptable salt thereof, as an active ingredient with conventional ophthalmically acceptable pharmaceutical excipients and by preparation of unit dosage suitable for topical ocular use. The therapeutically efficient amount typically is between about 0.0001 and about 5% (w/v), preferably about 0.001 to about 2.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional pharmaceutically acceptable preservatives, stabilizers and surfactants. Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar manner an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edetate disodium, although other chelating agents may also be used in place of or in conjunction with it.

The ingredients are usually used in the following amounts:
Ingredient Amount (% w/v)
active ingredient about 0.001-5
preservative 0-0.10
vehicle 0-40
tonicity adjustor 0-10
buffer 0.01-10
antioxidant as needed
surfactant as needed
q.s. with purified water and/or pH adjustor (pH 4.5-7.8) to make 100%

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for drop wise application are usually made of suitable inert, non-toxic plastic material, and generally contain between about 0.5 and about 15 ml solution. One package may contain one or more unit doses. Especially preservative-free solutions are often formulated in non-resealable containers containing up to about ten, preferably up to about five units doses, where a typical unit dose is from one to about 8 drops, preferably one to about 3 drops. The volume of one drop usually is about 20-35 microliters.

Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions which are responsive to treatment by agonists or functional antagonists of sphingosine-1-phosphate receptors. Thus, in further embodiments of the invention, there are provided methods for treating a disorder associated with modulation of sphingosine-1-phosphate receptors. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I. The compounds of Formula I according to the invention can be prepared analogously to conventional methods as understood by the person skilled in the art of synthetic organic chemistry. The synthetic scheme set forth below illustrates how compounds according to the invention can be made.

Scheme 1

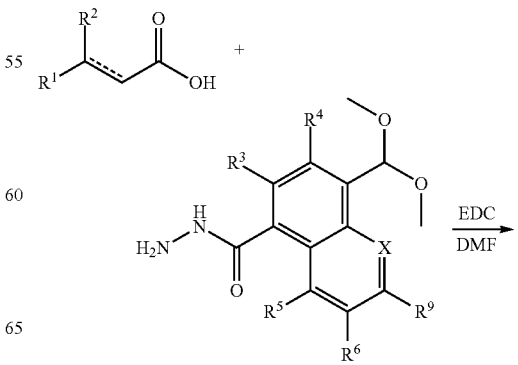

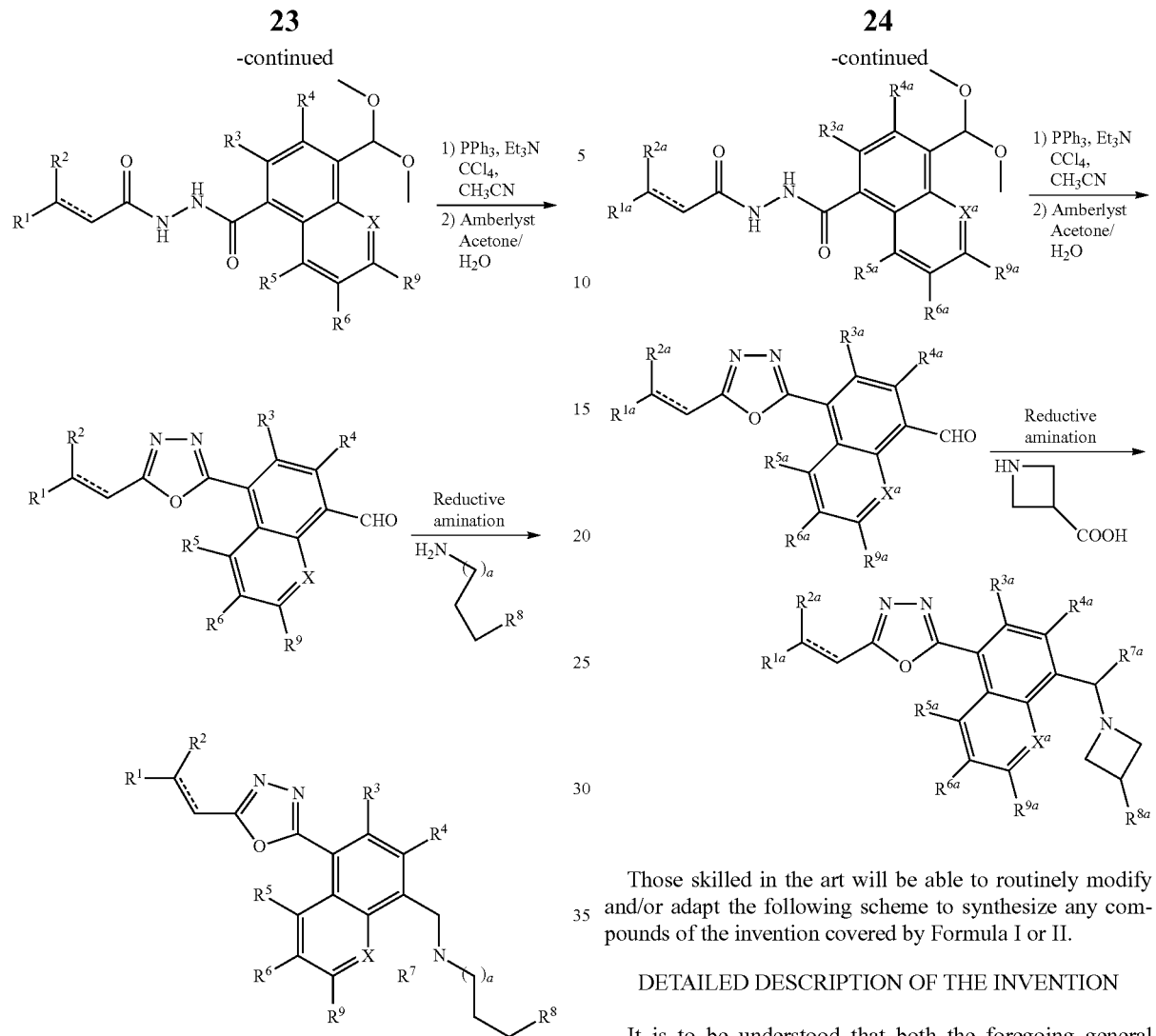

The present invention concerns also processes for preparing the compounds of Formula II. The compounds of Formula II according to the invention can be prepared analogously to conventional methods as understood by the person skilled in the art of synthetic organic chemistry. The synthetic scheme set forth below, illustrate how compounds according to the invention can be made.

Scheme 2

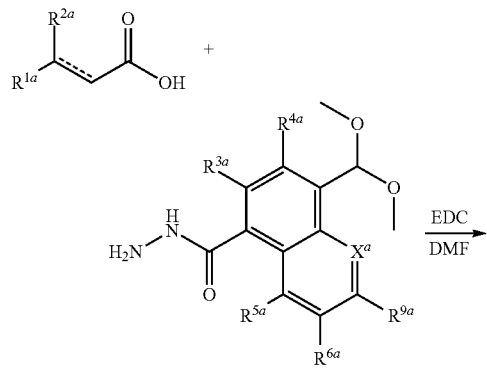

Those skilled in the art will be able to routinely modify and/or adapt the following scheme to synthesize any compounds of the invention covered by Formula I or II.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2$H (or D) in place of protium $^1$H (or H) or use of $^{13}$C-enriched material in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual diastereomeric forms can be obtained by separation of mixtures thereof in conventional manner; chromatographic separation may be employed.

Compound names were generated with ACDLab version 12.5; Intermediates and reagent names used in the examples were generated with software such as Chem Bio Draw Ultra version 12.0 or Auto Nom 2000 from MDL ISIS Draw 2.5 SP1.

In general, characterization of the compounds was performed according to the following methods: NMR spectra were recorded on 300 and/or 600 MHz Varian and acquired at room temperature. Chemical shifts are given in ppm referenced either to internal TMS or to the solvent signal.

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, AK Scientific, AmFine Com, Carbocore, Maybridge, Frontier, Matrix, Ukrorgsynth, Toronto, Ryan Scientific, Sili-Cycle, Anaspec, Syn Chem, Chem-Impex, MIC-scientific, Ltd; however some known intermediates were prepared according to published procedures.

Usually, the compounds of the invention were purified by column chromatography (Auto-column) on an Teledyne-ISCO CombiFlash with a silica column, unless noted otherwise.

The following abbreviations are used in the examples:
EDC 1-ethyl-3-(3-dimethylaminopropyl) carbodiimide
CD$_3$OD deuterated methanol
RT room temperature
CDCl$_3$ deuterated chloroform
MPLC medium pressure liquid chromatography
DMF dimethylformamide
NaHCO$_3$ sodium bicarbonate
PPh$_3$ triphenylphosphine
CCl$_4$ carbon tetrachloride
CH$_3$CN acetonitrile
TMS tetramethylsilane Those skilled in the art will be able to routinely modify and/or adapt the following schemes to synthesize any compound of the invention covered by Formula I or II.

Some compounds of this invention can generally be prepared in one step from commercially available literature starting materials.

Example 1

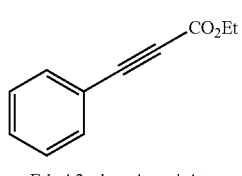

Intermediate 1

Ethyl 3-phenylpropiolate

To a solution of 3-phenylpropiolic acid (5 g, 49 mmol) in THF (50 mL) at −78° C. was added n-butyllithium (2.5M, 33 mL, 81 mmol) dropwise. The resulting mixture was stirred at 0° C. for 30 min and then cooled back to −78° C. Ethyl chloroformate (6.7 mL, 70 mmol) was added dropwise. The reaction mixture was stirred at from −78° C. to RT for 16 h. The reaction was quenched with sodium bicarbonate (sat.) and ammonium chloride (sat.) (1:1). The mixture was extracted with ethyl acetate. Combined ethyl acetate extracts were washed with water and brine, dried over magnesium sulfate, and concentrated. Purification of the residue by MPLC (2% ethyl acetate in hexanes) gave 4.6 g of Intermediate 1 as a yellow oil.

$^1$H NMR (600 MHz, CDCl$_3$) δ: 7.59 (dd, J=8.0, 1.0 Hz, 2H), 7.42-7.47 (m, 1H), 7.35-7.40 (m, 2H), 4.30 (q, J=7.1 Hz, 2H), 1.36 (t, J=7.2 Hz, 3H).

Example 2

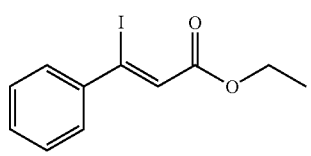

Intermediate 2

(Z)-Ethyl 3-iodo-3-phenylacrylate

To a solution of Intermediate 1 (4.6 g, 26.4 mmol) in acetic acid (22 mL) was added sodium iodide (13 g, 87 mmol). The reaction mixture was purged with argon and heated at 115° C. with a reflux condenser for 4 h. The reaction mixture was cooled to RT and diluted with water. The mixture was extracted with ether. Combined ether extracts were washed with sodium carbonate (sat.), sodium thiosulfate (sat.), brine, then dried over magnesium sulfate, and concentrated to yield 7.55 g Intermediate 2 as a yellow oil.

$^1$H NMR (600 MHz, CDCl$_3$) δ: 7.50-7.55 (m, 2H), 7.33-7.38 (m, 3H), 6.63 (s, 1H), 4.25-4.33 (m, 2H), 1.30-1.38 (m, 3H).

Example 3

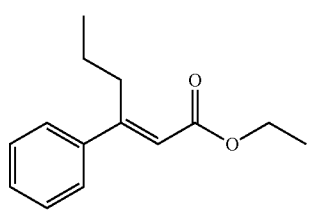

Intermediate 3

(E)-Ethyl 3-phenylhex-2-enoate

To a solution of Intermediate 2 (2.81 g, 9.3 mmol) in DMF (20 mL) under argon at 0° C. was added n-propyl zinc bromide (55 mL, 27.5 mmol) followed by bis(acetonitrile) dichloropalladium (361 mg, 137 mmol). The reaction mixture was stirred at RT for 16 h and diluted with ether, washed with HCl (10%), brine, dried over magnesium sulfate and concentrated. Purification of the residue by MPLC (10% ethyl acetate in hexanes) gave 1.6 g of Intermediate 3 as a yellow oil.

$^1$H NMR (600 MHz, CDCl$_3$) δ: 7.40-7.45 (m, 2H), 7.34-7.40 (m, 3H), 6.03 (s, 1H), 4.21 (q, J=7.1 Hz, 2H), 3.04-3.12 (m, 2H), 1.41-1.50 (m, 2H), 1.28-1.37 (m, 3H), 0.90-0.95 (m, 3H).

Intermediate 4 was prepared from Intermediate 2, in a similar manner to the procedure described in Example 3 for Intermediate 3. The results are tabulated below in Table 1.

TABLE 1

| Interm. No. | Structure IUPAC Name | $^1$H NMR δ (ppm) |
|---|---|---|
| 4 | (E)-ethyl 3-phenylhept-2-enoate | $^1$H NMR (600 MHz, CDCl$_3$) δ: 7.40-7.46 (m, 2H), 7.33-7.40 (m, 3H), 6.01 (s, 1H), 4.21 (q, J = 7.1 Hz, 2H), 3.05-3.13 (m, 2H), 1.34-1.45 (m, 4H), 1.29-1.34 (m, 3H), 0.88 (t, J = 7.2 Hz, 3H). |

Example 4

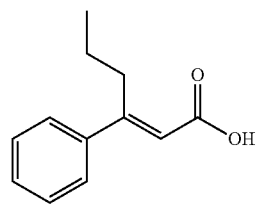

Intermediate 5

(E)-3-phenylhex-2-enoic acid

To the solution of intermediate 3 (1.6 g, 7.3 mmol) in dioxane (13 mL) and water (26 mL) was added KOH (1.48 g, 26.6 mmol). The reaction mixture was refluxed for 16 h, then cooled to RT, diluted with water, and HCl (10%) was added to achieve solution pH 2. The mixture was extracted with ethyl acetate. Combined ethyl acetate was washed with water and brine, dried over magnesium sulfate, and concentrated. Purification of the residue by MPLC (50% ethyl acetate in hexanes) gave 903 mg of Intermediate 5 as a white solid.

$^1$H NMR (600 MHz, CDCl$_3$) δ: 7.42-7.48 (m, 2H), 7.35-7.41 (m, 3H), 6.07 (s, 1H), 3.07-3.15 (m, 2H), 1.43-1.52 (m, 2H), 0.94 (t, J=7.3 Hz, 3H).

Intermediate 6 was prepared from the Intermediate 4 in a similar manner to the procedure described in Example 4 for Intermediate 5. The results are tabulated below in Table 2.

TABLE 2

| Interm. No. | Structure IUPAC Name | Interm. No. | $^1$H NMR δ (ppm) |
|---|---|---|---|
| 6 | 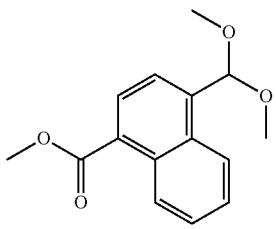 (E)-3-phenylhept-2-enoic acid | 4 | $^1$H NMR (600 MHz, CDCl$_3$) δ: 7.42-7.48 (m, 2H), 7.36-7.41 (m, 3H), 6.06 (s, 1H), 3.10-3.16 (m, 2H), 1.32-1.46 (m, 4H), 0.88 (t, J = 7.2 Hz, 3H). |

Example 5

Intermediate 7 methyl 4-(dimethoxymethyl)-1-naphthoate

A mixture of methyl 4-formyl-1-naphthoate (CAS #62855-40-7; 3.95 g, 19.7 mmol, 1.0 eq), trimethyl orthoformate (6.25 g, 59.1 mmol), and p-toluenesulfonic acid (0.23 g, 1.2 mmol, 0.06 eq) in MeOH (80 mL) was heated at reflux under nitrogen for 5 h, and then cooled to 5° C. followed by addition of 0.9% aq Na$_2$CO$_3$ (100 mL) to pH~7-8. The resulted mixture was stirred with ethyl acetate (200 mL) and the organic phase was separated. The aqueous phase was extracted with ethyl acetate (100 mL). Combined ethyl acetate extracts were washed with water and brine, dried over magnesium sulfate, and concentrated. Purification of the residue by MPLC (ethyl acetate in hexanes) gave 4.7 g (92.2%) Intermediate 7.

Intermediate 8, shown in Table 3, was prepared from the methyl 8-formylquinoline-5-carboxylate (CAS #260796-30-3) in a similar manner to the procedure described in Example 5 for Intermediate 7.

TABLE 3

| Interm. No. | Structure IUPAC Name |
|---|---|
| 8 | methyl 8-(dimethoxymethyl)quinoline-5-carboxylate |

Example 6

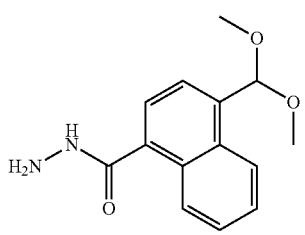

Intermediate 9

4-(dimethoxymethyl)-1-naphthohydrazide

To Intermediate 7 (3.15 g, 12.1 mmol, 1.0 eq) in MeOH (35 mL) was added hydrazine hydrate (6.1 g, 121 mmol, 10.0 eq). The mixture was heated at reflux for 4 h. The mixture was cooled to RT and concentrated. Purification by chromatography (EtOAc/Hexane) afforded 2 g (63.4%) Intermediate 9.

Intermediate 10, shown in Table 4, was prepared from Intermediates 8 in a similar manner to the procedure described in Example 6 for Intermediate 9. The results are tabulated below in Table 4.

TABLE 4

| Interm. No. | Structure IUPAC Name |
|---|---|
| 10 | ![structure] 8-(dimethoxymethyl) quinoline-5-carbohydrazide |

Example 7

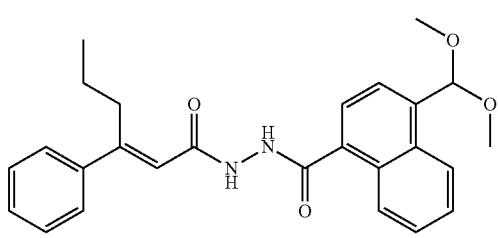

Intermediate 11

(E)-4-(dimethoxymethyl)-N'-(3-phenylhex-2-enoyl)-1-naphthohydrazide

To a solution of intermediate 5 (418 mg, 2.2 mmol) and Intermediate 9 (572 mg, 2.2 mmol) in DMF (30 mL) was added EDC (549 mg, 2.86 mmol). The reaction mixture was stirred at RT for 16 h. The mixture was then poured onto NaHCO₃ (10%) and extracted with ethyl acetate. Combined ethyl acetate extracts were washed with water and brine, dried over magnesium sulfate, and concentrated. Purification of the residue by MPLC (30% ethyl acetate in hexanes) gave 720 mg of intermediate 11 as a white solid.

$^1$H NMR (600 MHz, CDCl$_3$) δ: 10.22 (d, J=6.16 Hz, 1H), 9.54 (d, J=6.16 Hz, 1H), 8.25-8.35 (m, 2H), 7.66-7.69 (m, 2H), 7.52 (ddd, J=1.17, 6.90, 8.36 Hz, 1H), 7.42 (ddd, J=1.17, 6.97, 8.29 Hz, 1H), 7.29-7.33 (m, 2H), 7.23-7.28 (m, 1H), 7.15-7.21 (m, 2H), 6.25 (s, 1H), 5.90 (s, 1H), 3.32 (s, 6H), 3.03-3.10 (m, 2H), 1.35-1.43 (m, 2H), 0.85 (t, J=7.34 Hz, 3H).

Intermediates 12 through 16, 23 and 24 were prepared from Intermediates 5, 6, 9, 10, 3-phenylhexanoic acid (CAS #5703-52-6), 3-phenylheptanoic acid (CAS #5638-30-2), and 3-phenyloctanoic acid (CAS #20966-57-8), as specified in Table 5, and in a similar manner to the procedure described in Example 7 for Intermediate 11. The results are tabulated below in Table 5.

TABLE 5

| Interm. No. | Structure IUPAC Name | Starting materials | $^1$H NMR δ (ppm) |
|---|---|---|---|
| 12 | ![structure] (E)-4-(dimethoxymethyl)-N'-(3-phenylhept-2-enoyl)-1-naphthohydrazide | Interm. 6 and 9 | $^1$H NMR (600 MHz, CDCl$_3$) δ: 8.41 (d, J = 8.22 Hz, 1H), 8.32 (d, J = 8.22 Hz, 1H), 7.75 (d, J = 4.11 Hz, 2H), 7.52-7.61 (m, 2H), 7.39-7.45 (m, 2H), 7.31-7.37 (m, 3H), 6.10 (s, 1H), 5.95 (s, 1H), 3.36 (s, 6H), 3.11-3.21 (m, 2H), 1.31-1.46 (m, 4H), 0.85-0.89 (m, 3H) |

TABLE 5-continued

| Interm. No. | Structure / IUPAC Name | Starting materials | $^1$H NMR δ (ppm) |
|---|---|---|---|
| 13 | (E)-8-(dimethoxymethyl)-N'-(3-phenylhex-2-enoyl)quinoline-5-carbohydrazide | Interm. 5 and 10 | $^1$H NMR (600 MHz, CDCl$_3$) δ 8.85 (dd, J = 1.61, 3.96 Hz, 1H), 8.58 (dd, J = 1.61, 8.66 Hz, 1H), 7.82 (d, J = 7.34 Hz, 1H), 7.74 (d, J = 7.34 Hz, 1H), 7.17-7.24 (m, 4H), 7.10-7.14 (m, 2H), 6.47 (s, 1H), 6.15 (s, 1H), 3.33 (s, 6H), 2.94-3.02 (m, 2H), 1.27-1.34 (m, 2H), 0.76 (t, J = 7.34 Hz, 3H) |
| 14 | (E)-8-(dimethoxymethyl)-N'-(3-phenylhept-2-enoyl)quinoline-5-carbohydrazide | Interm. 6 and 10 | $^1$H NMR (600 MHz, CDCl$_3$) δ 9.01 (dd, J = 1.61, 3.96 Hz, 1H), 8.82 (d, J = 8.51 Hz, 1H), 7.99 (d, J = 7.34 Hz, 1H), 7.88 (d, J = 7.34 Hz, 1H), 7.38-7.44 (m, 3H), 7.32-7.37 (m, 3H), 6.60 (s, 1H), 6.07 (s, 1H), 3.45 (s, 6H), 3.12-3.19 (m, 2H), 1.28-1.47 (m, 4H), 0.87 (t, J = 7.34 Hz, 4H) |
| 15 | 4-(dimethoxymethyl)-N'-(3-phenyloctanoyl)-1-naphthohydrazide | Interm. 9 and 3-phenyl-octanoic acid | N/A |
| 16 | 8-(dimethoxymethyl)-N'-(3-phenylhexanoyl)quinoline-5-carbohydrazide | Interm. 10 and 3-phenyl-hexanoic acid | N/A |

TABLE 5-continued

| Interm. No. | Structure IUPAC Name | Starting materials | $^1$H NMR δ (ppm) |
|---|---|---|---|
| 23 | 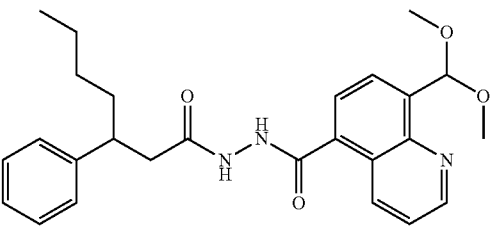<br>8-(dimethoxymethyl)-N'-(3-phenylheptanoyl)quinoline-5-carbohydrazide | Intermed. 10 and 3-phenyl-heptanoic acid | N/A |
| 24 | 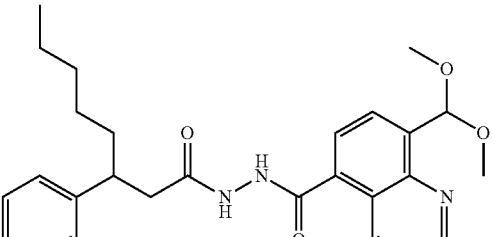<br>8-(dimethoxymethyl)-N'-(3-phenyloctanoyl)quinoline-5-carbohydrazide | Intermed. 10 and 3-phenyl-octanoic acid | N/A |

Example 8

Intermediate 17

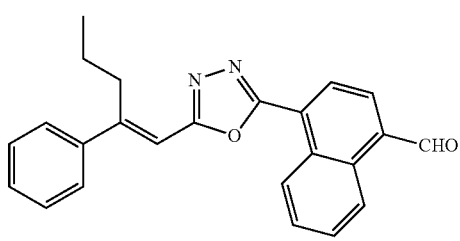

(E)-4-(5-(2-phenylpent-1-en-1-yl)-1,3,4-oxadiazol-2-yl)-1-naphthaldehyde

A solution of Intermediate 11 ((E)-4-(dimethoxymethyl)-N'-(3-phenylhex-2-enoyl)-1-naphthohydrazide; 760 mg, 1.66 mol), triphenylphosphine (873 mg, 3.33 mmol), triethylamine (0.83 mL, 6 mmol) and carbon tetrachloride (0.58 mL, 6 mmol) in acetonitrile (30 mL) was stirred at RT for 16 h. The acetonitrile was removed and the residue was taken up in ethyl acetate. The ethyl acetate was washed with water and brine, dried over magnesium sulfate, and concentrated to give a crude mixture. The mixture was dissolved in acetone (30 mL):water (0.6 mL) and Amberlyst (0.5 g) was added. After stirring for 2 hr, the reaction was filtered and concentrated. Purification by MPLC (25% ethyl acetate in hexanes) gave 476 mg of Intermediate 17 as a white solid.

$^1$H NMR (600 MHz, CDCl$_3$) δ: 10.44 (s, 1H), 9.36-9.47 (m, 1H), 9.24 (d, J=9.68 Hz, 1H), 8.24 (d, J=7.63 Hz, 1H), 8.01 (d, J=7.34 Hz, 1H), 7.66-7.80 (m, 2H), 7.49-7.61 (m, 2H), 7.31-7.46 (m, 3H), 6.69 (s, 1H), 3.18-3.29 (m, 2H), 1.57-1.69 (m, 2H), 1.04 (t, J=7.34 Hz, 3H).

Intermediates 18 through 22, 25 and 26 were prepared from Intermediates 12 through 16, 23 and 24 in a similar manner to the procedure described in Example 8 for Intermediate 17. The results are tabulated below in Table 6.

TABLE 6

| Interm. No. | Structure IUPAC Name | Starting Interm. | ¹H NMR δ (ppm) |
|---|---|---|---|
| 18 | (E)-4-(5-(2-phenylhex-1-en-1-yl)-1,3,4-oxadiazol-2-yl)-1-naphthaldehyde | 12 | ¹H NMR (600 MHz, CDCl₃) δ 10.51 (s, 1H), 9.38-9.51 (m, 1H), 9.24-9.35 (m, 1H), 8.32 (d, J = 7.63 Hz, 1H), 8.09 (d, J = 7.63 Hz, 1H), 7.74-7.88 (m, 2H), 7.53-7.64 (m, 2H), 7.36-7.48 (m, 3H), 6.71 (s, 1H), 3.21-3.33 (m, 2H), 1.55-1.62 (m, 2H), 1.39-1.53 (m, 2H), 0.94 (t, J = 7.34 Hz, 3H) |
| 19 | (E)-5-(5-(2-phenylpent-1-en-1-yl)-1,3,4-oxadiazol-2-yl)quinoline-8-carbaldehyde | 13 | ¹H NMR (600 MHz, CDCl₃) δ 11.54 (s, 1H), 9.95 (dd, J = 1.76, 8.80 Hz, 1H), 9.16 (dd, J = 1.76, 4.11 Hz, 1H), 8.40-8.47 (m, 1H), 8.36-8.39 (m, 1H), 7.71 (dd, J = 4.11, 8.80 Hz, 1H), 7.57 (dd, J = 1.47, 8.22 Hz, 2H), 7.38-7.48 (m, 3H), 6.73 (s, 1H), 3.20-3.31 (m, 2H), 1.60-1.70 (m, 2H), 1.05 (t, J = 7.34 Hz, 3H) |
| 20 | (E)-5-(5-(2-phenylhex-1-en-1-yl)-1,3,4-oxadiazol-2-yl)quinoline-8-carbaldehyde | 14 | ¹H NMR (600 MHz, CDCl₃) δ: 11.53 (d, J = 0.88 Hz, 1H), 9.93 (dd, J = 1.76, 8.80 Hz, 1H), 9.15 (dd, J = 1.76, 4.11 Hz, 1H), 8.38-8.43 (m, 1H), 8.34-8.37 (m, 1H), 7.70 (dd, J = 4.11, 8.80 Hz, 1H), 7.53-7.59 (m, 2H), 7.41-7.48 (m, 3H), 6.71 (s, 1H), 3.24-3.33 (m, 2H), 1.55-1.62 (m, 2H), 1.44-1.53 (m, 2H), 0.94 (t, J = 7.34 Hz, 3H) |
| 21 | 4-(5-(2-phenylheptyl)-1,3,4-oxadiazol-2-yl)-1-naphthaldehyde | 15 | ¹H NMR (600 MHz, CDCl₃) δ 10.50 (s, 1H), 9.27 (d, J = 8.51 Hz, 1H), 9.08 (d, J = 8.51 Hz, 1H), 7.98-8.09 (m, 2H), 7.76 (dt, J = 1.17, 7.63 Hz, 1H), 7.69-7.74 (m, 1H), 7.29-7.35 (m, 2H), 7.21-7.27 (m, 3H), 3.33-3.43 (m, 1H), 3.17-3.29 (m, 2H), 1.74-1.89 (m, 2H), 1.16-1.38 (m, 6H), 0.77-0.89 (m, 3H) |

TABLE 6-continued

| Interm. No. | Structure / IUPAC Name | Starting Interm. | $^1$H NMR δ (ppm) |
|---|---|---|---|
| 22 | 5-(5-(2-phenylpentyl)-1,3,4-oxadiazol-2-yl)quinoline-8-carbaldehyde | 16 | $^1$H NMR (600 MHz, CDCl$_3$) δ 11.48 (s, 1H), 9.60 (dd, J = 1.47, 8.80 Hz, 1H), 9.10 (dd, J = 1.32, 3.96 Hz, 1H), 8.32 (d, J = 7.63 Hz, 1H), 8.06 (d, J = 7.63 Hz, 1H), 7.62 (dd, J = 4.11, 8.80 Hz, 1H), 7.29-7.34 (m, 2H), 7.22-7.26 (m, 3H), 3.32-3.42 (m, 1H), 3.19-3.30 (m, 2H), 1.80 (q, J = 7.24 Hz, 2H), 1.18-1.34 (m, 2H), 0.90 (t, J = 7.34 Hz, 3H) |
| 25 | 5-(5-(2-phenylhexyl)-1,3,4-oxadiazol-2-yl)quinoline-8-carbaldehyde | 23 | $^1$H NMR (600 MHz, CDCl$_3$) δ 11.46 (br. s., 1H), 9.58 (br. s., 1H), 8.98-9.22 (m, 1H), 8.20-8.45 (m, 1H), 7.95-8.12 (m, 1H), 7.60 (d, J = 2.93 Hz, 1H), 7.30-7.35 (m, 2H), 7.25 (d, J = 7.34 Hz, 3H), 3.33-3.46 (m, 1H), 3.17-3.31 (m, 2H), 1.76-1.92 (m, 2H), 1.10-1.41 (m, 4H), 0.77-0.95 (m, 3H) |
| 26 | 5-(5-(2-phenylheptyl)-1,3,4-oxadiazol-2-yl)quinoline-8-carbaldehyde | 24 | $^1$H NMR (600 MHz, CDCl$_3$) δ 11.50 (s, 1H), 11.43-11.55 (m, 1H), 9.63 (dd, J = 1.47, 8.80 Hz, 1H), 9.12 (dd, J = 1.61, 3.96 Hz, 1H), 8.34 (d, J = 7.63 Hz, 1H), 8.08 (d, J = 7.63 Hz, 1H), 7.65 (dd, J = 4.11, 8.80 Hz, 1H), 7.30-7.34 (m, 2H), 7.21-7.27 (m, 3H), 3.32-3.45 (m, 1H), 3.18-3.29 (m, 2H), 1.80 (d, J = 7.04 Hz, 2H), 1.14-1.38 (m, 6H), 0.77-0.92 (m, 3H) |

Example 9

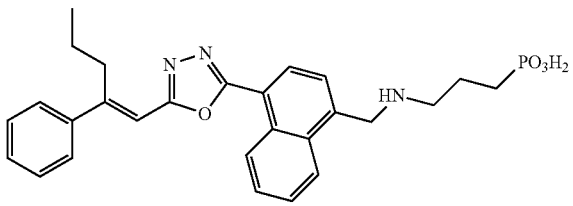

Compound 1

(3-{[(4-{5-[(1E)-2-phenylpent-1-en-1-yl]-1,3,4-oxadiazol-2-yl}naphthalen-1-yl)methyl]amino} propyl)phosphonic acid To a solution of Intermediate 17, (E)-4-(5-(2-phenylpent-1-en-1-yl)-1,3,4-oxadiazol-2-yl)-1-naphthaldehyde (205 mg, 0.55 mmol) and (3-aminopropyl)phosphonic acid (77 mg, 0.55 mmol) in methanol (10 mL) was added tetrabutylammonium hydroxide (1 M in MeOH, 0.55 mL). The reaction mixture was heated to 50° C. for 1 h with stirring, cooled to RT, then sodium borohydride (31 mg, 0.82 mmol) was added. After the reaction mixture was stirred at RT for 3 h, the mixture was concentrated and purified by MPLC (100% methanol in ethyl acetate) to give 213 mg of Compound 1 as a colorless solid.

$^1$H NMR (600 MHz, CD$_3$OD) δ: 9.21-9.31 (m, 1H), 8.26-8.37 (m, 2H), 7.87 (d, J=7.63 Hz, 1H), 7.82-7.85 (m, 2H), 7.61-7.66 (m, 2H), 7.39-7.50 (m, 3H), 6.77 (s, 1H), 4.85 (s, 2H), 3.35-3.40 (m, 2H), 3.25-3.29 (m, 2H), 2.11 (td, J=7.74, 15.33 Hz, 2H), 1.87 (td, J=7.59, 18.56 Hz, 2H), 1.57-1.67 (m, 2H), 1.03 (t, J=7.48 Hz, 3H).

Compounds 2 through 12, and 19 through 22 were prepared from Intermediates 17 through 22, 25 and 26 in a similar manner to the procedure described in Example 9 for Compound 1, and as specified in Table 7. The results are tabulated below in Table 7.

TABLE 7

| Comp No. | Structure IUPAC Name | Starting Interm. | $^1$H NMR δ (ppm) |
|---|---|---|---|
| 2 | 3-{[(4-{5-[(1E)-2-phenylpent-1-en-1-yl]-1,3,4-oxadiazol-2-yl}naphthalen-1-yl)methyl]amino}propanoic acid | 17 | $^1$H NMR (600 MHz, CD$_3$OD) δ: 9.17-9.27 (m, 1H), 8.28-8.35 (m, 1H), 8.23 (d, J = 7.34 Hz, 1H), 7.72-7.83 (m, 3H), 7.63 (d, J = 7.04 Hz, 2H), 7.39-7.50 (m, 3H), 6.76 (s, 1H), 4.58 (s, 2H), 3.24-3.28 (m, 2H), 3.19 (br., 2H), 2.53 (t, J = 6.46 Hz, 2H), 1.55-1.68 (m, 2H), 1.03 (t, J = 7.34 Hz, 3H) |
| 3 | (3-{[(4-{5-[(1E)-2-phenylhex-1-en-1-yl]-1,3,4-oxadiazol-2-yl}naphthalen-1-yl)methyl]amino}propyl)phosphonic acid | 18 | $^1$H NMR (600 MHz, CD$_3$OD) δ: 9.23-9.31 (m, 1H), 8.26-8.36 (m, 2H), 7.79-7.91 (m, 3H), 7.63 (d, J = 7.34 Hz, 2H), 7.38-7.50 (m, 3H), 6.76 (s, 1H), 4.85 (s, 2H), 3.34-3.41 (m, 2H), 3.27-3.31 (m, 2H), 2.11 (td, J = 7.52, 15.19 Hz, 2H), 1.87 (td, J = 7.48, 18.49 Hz, 2H), 1.57 (t, J = 7.78 Hz, 2H), 1.43-1.51 (m, 2H), 0.93 (t, J = 7.34 Hz, 3H) |

TABLE 7-continued

| Comp No. | Structure / IUPAC Name | Starting Interm. | $^1$H NMR δ (ppm) |
|---|---|---|---|
| 4 | 3-{[(4-{5-[(1E)-2-phenylhex-1-en-1-yl]-1,3,4-oxadiazol-2-yl}naphthalen-1-yl)methyl]amino}propanoic acid | 18 | $^1$H NMR (600 MHz, CD$_3$OD) δ: 9.12-9.23 (m, 1H), 8.23-8.33 (m, 1H), 8.16 (d, J = 7.63 Hz, 1H), 7.67-7.78 (m, 3H), 7.55-7.63 (m, 2H), 7.37-7.51 (m, 3H), 6.71 (s, 1H), 4.47 (s, 2H), 3.21-3.28 (m, 2H), 3.12 (t, J = 6.46 Hz, 2H), 2.52 (t, J = 6.46 Hz, 2H), 1.50-1.58 (m, 2H), 1.41-1.49 (m, 2H), 0.92 (t, J = 7.34 Hz, 3H) |
| 5 | 3-{[(5-{5-[(1E)-2-phenylpent-1-en-1-yl]-1,3,4-oxadiazol-2-yl}quinolin-8-yl)methyl]amino}propyl) phosphonic acid | 19 | $^1$H NMR (600 MHz, CD$_3$OD) δ: 9.75-9.84 (m, 1H), 9.09-9.18 (m, 1H), 8.38 (d, J = 7.63 Hz, 1H), 8.07 (d, J = 7.34 Hz, 1H), 7.84 (dd, J = 4.25, 8.66 Hz, 1H), 7.63 (d, J = 7.04 Hz, 2H), 7.38-7.51 (m, 3H), 6.78 (s, 1H), 4.87 (s, 2H), 3.27-3.30 (m, 4H), 2.05-2.20 (m, 2H), 1.80-1.92 (m, 2H), 1.63 (d, J = 7.63 Hz, 2H), 1.04 (t, J = 7.34 Hz, 3H) |
| 6 | 3-{[(5-{5-[(1E)-2-phenylpent-1-en-1-yl]-1,3,4-oxadiazol-2-yl}quinolin-8-yl)methyl]amino}propanoic acid | 19 | $^1$H NMR (600 MHz, CD$_3$OD) δ: 9.66-9.76 (m, 1H), 9.08-9.17 (m, 1H), 8.26-8.39 (m, 1H), 7.95-8.06 (m, 1H), 7.73-7.85 (m, 1H), 7.62 (d, J = 7.92 Hz, 2H), 7.37-7.50 (m, 3H), 6.76 (br. s., 1H), 4.78 (s, 2H), 3.23-3.30 (m, 4H), 2.56 (t, J = 6.16 Hz, 2H), 1.55-1.69 (m, 2H), 1.03 (t, J = 7.34 Hz, 3H) |
| 7 | (3-{[(5-{5-[(1E)-2-phenylhex-1-en-1-yl]-1,3,4-oxadiazol-2-yl}quinolin-8-yl)methyl]amino}propyl) phosphonic acid | 20 | $^1$H NMR (600 MHz, CD$_3$OD) δ: 9.78 (dd, J = 1.76, 8.80 Hz, 1H), 9.14 (dd, J = 1.76, 4.11 Hz, 1H), 8.38 (d, J = 7.34 Hz, 1H), 8.07 (d, J = 7.34 Hz, 1H), 7.84 (dd, J = 4.11, 8.80 Hz, 1H), 7.63 (dd, J = 1.32, 8.36 Hz, 2H), 7.38-7.52 (m, 3H), 6.76 (s, 1H), 4.87 (s, 2H), 3.28-3.32 (m, 4H), 2.02-2.21 (m, 2H), 1.79-1.94 (m, 2H), 1.54-1.61 (m, 2H), 1.44-1.51 (m, 2H), 0.94 (t, J = 7.34 Hz, 2H) |

TABLE 7-continued

| Comp No. | Structure IUPAC Name | Starting Interm. | ¹H NMR δ (ppm) |
|---|---|---|---|
| 8 | 3-{[(5-{5-[(1E)-2-phenylhex-1-en-1-yl]-1,3,4-oxadiazol-2-yl}quinolin-8-yl)methyl]amino}propanoic acid | 20 | ¹H NMR (600 MHz, CD$_3$OD) δ: 9.73 (dd, J = 1.32, 8.66 Hz, 1H), 9.15 (dd, J = 1.32, 4.25 Hz, 1H), 8.34 (d, J = 7.34 Hz, 1H), 8.03 (d, J = 7.34 Hz, 1H), 7.80 (dd, J = 4.11, 8.51 Hz, 1H), 7.62 (d, J = 7.04 Hz, 2H), 7.38-7.53 (m, 3H), 6.75 (s, 1H), 4.80 (s, 2H), 3.27-3.30 (m, 4H), 2.57 (t, J = 6.02 Hz, 2H), 1.52-1.60 (m, 2H), 1.43-1.51 (m, 2H), 0.93 (t, J = 7.34 Hz, 3H) |
| 9 | {3-[({4-[5-(2-phenylheptyl)-1,3,4-oxadiazol-2-yl]naphthalen-1-yl}methyl)amino]propyl}phosphonic acid | 21 | ¹H NMR (600 MHz, CD$_3$OD) δ: 8.82 (d, J = 8.51 Hz, 1H), 8.27 (d, J = 8.51 Hz, 1H), 8.00 (d, J = 7.34 Hz, 1H), 7.77-7.82 (m, 2H) 7.71-7.76 (m, 1H), 7.24-7.33 (m, 4H), 7.19-7.23 (m, 1H), 4.81 (s, 2H), 3.39-3.44 (m, 1H), 3.33-3.37 (m, 2H), 3.20-3.27 (m, 2H), 2.03-2.17 (m, 2H), 1.79-1.93 (m, 4H), 1.19-1.37 (m, 6H), 0.85 (t, J = 6.90 Hz, 3H) |
| 10 | 3-[({4-[5-(2-phenylheptyl)-1,3,4-oxadiazol-2-yl]naphthalen-1-yl}methyl)amino]propanoic acid | 21 | ¹H NMR (600 MHz, CD$_3$OD) δ: 8.76-8.83 (m, 1H), 8.21-8.30 (m, 1H), 7.90-7.99 (m, 1H), 7.74 (t, J = 6.90 Hz, 2H), 7.69 (d, J = 7.34 Hz, 1H), 7.24-7.32 (m, 4H), 7.20 (s, 1H), 4.65 (s, 2H), 3.36-3.42 (m, 1H), 3.25 (t, J = 7.19 Hz, 4H), 2.54 (t, J = 6.31 Hz, 2H), 1.72-1.94 (m, 2H), 1.09-1.39 (m, 6H), 0.85 (t, J = 6.60 Hz, 3H) |
| 11 | {3-[({5-[5-(2-phenylpentyl)-1,3,4-oxadiazol-2-yl]quinolin-8-yl}methyl)amino]propryl}phosphonic acid | 22 | ¹H NMR (600 MHz, CD$_3$OD) δ: 9.37 (d, J = 8.80 Hz, 1H), 9.04-9.12 (m, 1H), 8.10 (d, J = 7.63 Hz, 1H), 8.01 (d, J = 7.34 Hz, 1H), 7.73 (dd, J = 4.25, 8.66 Hz, 1H), 7.24-7.31 (m, 4H), 7.17-7.22 (m, 1H), 4.78 (s, 2H), 3.38-3.43 (m, 1H), 3.23-3.29 (m, 2H), 3.21 (t, J = 6.46 Hz, 2H), 2.04 (td, J = 6.86, 17.97 Hz, 2H), 1.78-1.88 (m, 2H), 1.66-1.77 (m, 2H), 1.19-1.36 (m, 2H), 0.92 (t, J = 7.34 Hz, 3H) |

TABLE 7-continued

| Comp No. | Structure<br>IUPAC Name | Starting Interm. | $^1$H NMR δ (ppm) |
|---|---|---|---|
| 12 | 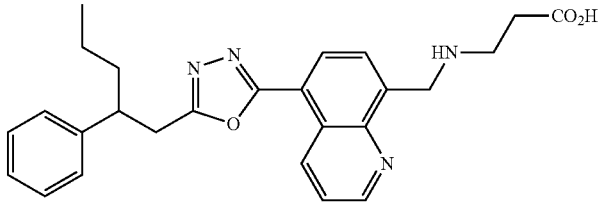<br>3-[({5-[5-(2-phenylpentyl)-1,3,4-oxadiazol-2-yl]quinolin-8-yl}methyl)amino]propanoic acid | 22 | $^1$H NMR (600 MHz, CD$_3$OD) δ: 9.29 (dd, J = 1.47, 8.80 Hz, 1H), 9.03-9.13 (m, 1H), 8.05 (d, J = 7.63 Hz, 1H), 7.93 (d, J = 7.34 Hz, 1H), 7.69 (dd, J = 4.40, 8.80 Hz, 1H), 7.24-7.31 (m, 4H), 7.17-7.22 (m, 1H), 4.74 (s, 2H), 3.37-3.44 (m, 1H), 3.32-3.36 (m, 1H), 3.25-3.27 (m, 3H), 2.55 (t, J = 6.02 Hz, 2H), 1.70-1.92 (m, 2H), 1.27 (dt, J = 7.48, 16.07 Hz, 2H), 0.91 (t, J = 7.48 Hz, 3H) |
| 19 | 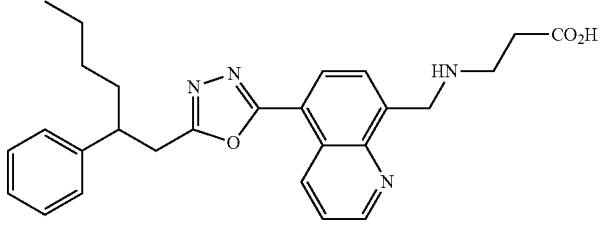<br>3-[({5-[5-(2-phenylhexyl)-1,3,4-oxadiazol-2-yl]quinolin-8-yl}methyl)amino]propanoic acid | 25 | $^1$H NMR (600 MHz, CD$_3$OD) δ 9.19 (dd, J = 1.17, 8.80 Hz, 1H), 8.95-9.03 (m, 1H), 7.95 (d, J = 7.34 Hz, 1H), 7.85 (d, J = 7.34 Hz, 1H), 7.58 (dd, J = 4.11, 8.80 Hz, 1H), 7.24-7.32 (m, 4H), 7.18-7.22 (m, 1H), 4.68 (s, 2H), 3.36-3.41 (m, 1H), 3.18-3.30 (m, 4H), 2.56 (t, J = 6.02 Hz, 2H), 1.70-1.94 (m, 2H), 1.09-1.45 (m, 4H), 0.85 (t, J = 7.04 Hz, 3H) |
| 20 | 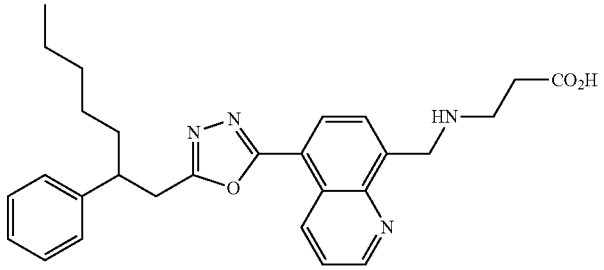<br>3-[({5-[5-(2-phenylheptyl)-1,3,4-oxadiazol-2-yl]quinolin-8-yl}methyl)amino]propanoic acid | 26 | $^1$H NMR (600 MHz, CD$_3$OD) δ 9.33 (ddd, J = 1.47, 8.80, 12.62 Hz, 1H), 9.10 (ddd, J = 1.47, 4.25, 8.07 Hz, 1H), 8.04-8.13 (m, 1H), 7.96 (t, J = 7.48 Hz, 1H), 7.72 (td, J = 4.62, 8.95 Hz, 1H), 7.24-7.32 (m, 4H), 7.19-7.23 (m, 1H), 4.76 (d, J = 7.04 Hz, 2H), 3.38-3.44 (m, 1H), 3.20-3.29 (m, 4H), 2.55 (t, J = 6.16 Hz, 2H), 1.75-1.95 (m, 2H), 1.11-1.40 (m, 6H), 0.85 (t, J = 6.31 Hz, 3H) |
| 21 | 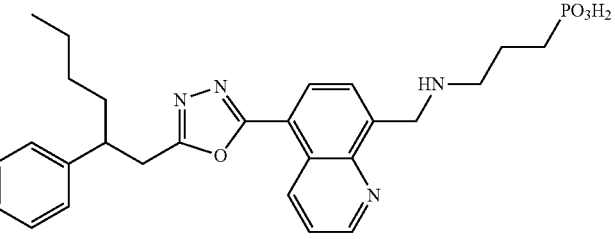<br>{3-[({5-[5-(2-phenylhexyl)-1,3,4-oxadiazol-2-yl]quinolin-8-yl}methyl)amino]propyl}phosphonic acid | 25 | $^1$H NMR (600 MHz, CD$_3$OD) δ 9.39 (dd, J = 1.47, 8.80 Hz, 1H), 9.09 (dd, J = 1.76, 4.11 Hz, 1H), 8.11 (d, J = 7.63 Hz, 1H), 8.00 (d, J = 7.63 Hz, 1H), 7.76 (dd, J = 4.11, 8.80 Hz, 1H), 7.24-7.32 (m, 4H), 7.18-7.23 (m, 1H), 4.83 (s, 2H), 3.39-3.46 (m, 1H), 3.20-3.29 (m, 4H), 2.10 (td, J = 7.26, 14.82 Hz, 2H), 1.77-1.93 (m, 4H), 1.13-1.47 (m, 4H), 0.87 (t, J = 7.19 Hz, 3H) |

TABLE 7-continued

| Comp No. | Structure IUPAC Name | Starting Interm. | $^1$H NMR δ (ppm) |
|---|---|---|---|
| 22 | 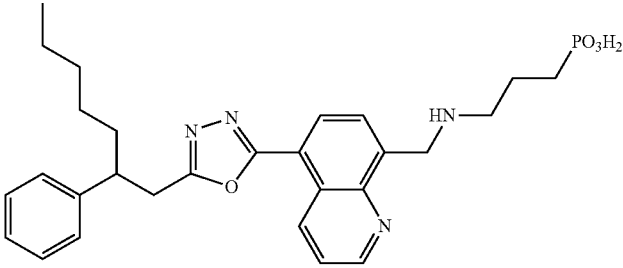{3-[({5-[5-(2-phenylheptyl)-1,3,4-oxadiazol-2-yl]quinolin-8-yl}methyl)amino]propyl}phosphonic acid | 26 | $^1$H NMR (600 MHz, CD$_3$OD) δ 9.39 (dd, J = 1.47, 8.80 Hz, 1H), 9.09 (dd, J = 1.47, 4.11 Hz, 1H), 8.12 (d, J = 7.34 Hz, 1H), 8.00 (d, J = 7.63 Hz, 1H), 7.76 (dd, J = 4.40, 8.80 Hz, 1H), 7.24-7.33 (m, 4H), 7.19-7.23 (m, 1H), 4.83 (s, 2H), 3.39-3.45 (m, 1H), 3.19-3.30 (m, 4H), 2.10 (td, J = 7.45, 14.75 Hz, 2H), 1.75-1.97 (m, 4H), 1.11-1.44 (m, 6H), 0.85 (t, J = 7.04 Hz, 3H) |

Example 9

Compound 13

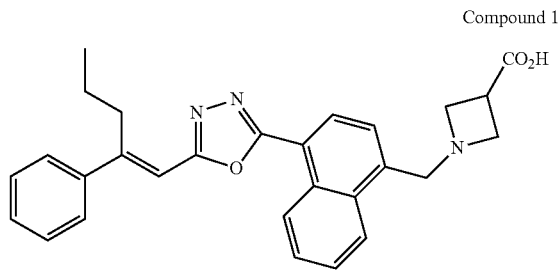

1-[(4-{5-[(1E)-2-phenylpent-1-en-1-yl]-1,3,4-oxadiazol-2-yl}naphthalen-1-yl)methyl]azetidine-3-carboxylic acid To a solution of Intermediate 17 (151 mg, 0.41 mmol) in methanol (10 mL) was added 3-azetidinecarboxylic acid ([CAS 36476-78-5] 45 mg, 0.45 mmol). After the reaction mixture was stirred at RT for 2.5 h, sodium borohydride (23 mg, 0.61 mmol) was added. After the mixture was stirred at RT for 1.5 h, the mixture was concentrated and purified by MPLC (100% methanol in ethyl acetate) to give 40 mg of Compound 13 as a colorless solid.

$^1$H NMR (600 MHz, CD$_3$OD) δ: 9.15-9.24 (m, 1H), 8.29 (dd, J=1.61, 7.78 Hz, 1H), 8.18 (d, J=7.34 Hz, 1H), 7.67-7.77 (m, 3H), 7.58-7.65 (m, 2H), 7.36-7.49 (m, 3H), 6.73 (s, 1H), 4.48 (s, 2H), 3.88 (t, J=8.95 Hz, 2H), 3.78 (t, J=8.51 Hz, 2H), 3.35 (s, 1H), 3.20-3.27 (m, 2H), 1.54-1.65 (m, 2H), 1.02 (t, J=7.34 Hz, 3H).

Compounds 14 through 18, 23 and 24 were prepared from the Intermediates 18 through 22, 25 and 26, in a similar manner to the procedure described in Example 9 for Compound 13, and as specified in Table 8. The results are tabulated below in Table 8.

TABLE 8

| Cmpd No. | Structure IUPAC Name | Starting Interm. | $^1$H NMR δ (ppm) |
|---|---|---|---|
| 14 | 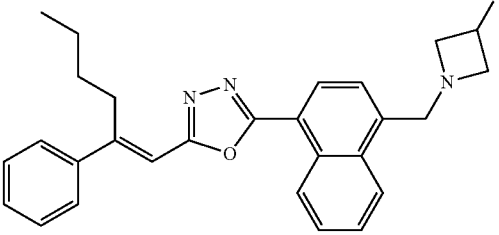1-[(4-{5-[(1E)-(2-phenylhex-1-en-1-yl]-1,3,4-oxadiazol-2-yl}naphthalen-1-yl)methyl]azetidine-3-carboxylic acid | 18 | $^1$H NMR (600 MHz, CD$_3$OD) δ: 9.10-9.22 (m, 1H), 8.19-8.31 (m, 1H), 8.09 (d, J = 7.63 Hz, 1H), 7.61-7.72 (m, 3H), 7.55 (d, J = 7.04 Hz, 2H), 7.35-7.45 (m, 3H), 6.63 (s, 1H), 4.50 (s, 2H), 3.90-4.02 (m, 2H), 3.78-3.88 (m, 2H), 3.34-3.37 (m, 1H), 3.12-3.23 (m, 2H), 1.34-1.54 (m, 4H), 0.88 (t, J = 7.34 Hz, 3H) |

TABLE 8-continued

| Cmpd No. | Structure IUPAC Name | Starting Interm. | $^1$H NMR δ (ppm) |
|---|---|---|---|
| 15 | (E)-1-((5-(5-(2-phenylpent-1-en-1-yl)-1,3,4-oxadiazol-2-yl)quinolin-8-yl)methyl]azetidine-3-carboxylic acid | 19 | $^1$H NMR (600 MHz, CD$_3$OD) δ: 9.67 (dd, J = 1.61, 8.66 Hz, 1H), 9.05 (dd, J = 1.47, 4.11 Hz, 1H), 8.27 (d, J = 7.34 Hz, 1H), 8.00 (d, J = 7.63 Hz, 1H), 7.74 (dd, J = 4.11, 8.51 Hz, 1H), 7.54-7.64 (m, 2H), 7.32-7.48 (m, 3H), 6.70 (s, 1H), 4.84 (s, 2H), 4.05-4.17 (m, 4H), 3.38-3.46 (m, 1H), 3.17-3.25 (m, 2H), 1.54-1.63 (m, 2H), 1.01 (t, J = 7.34 Hz, 3H) |
| 16 | 1-[(5-{5-[(1E)-2-phenylhex-1-en-1-yl]-1,3,4-oxadiazol-2-yl}quinolin-8-yl)methyl]azetidine-3-carboxylic acid | 20 | $^1$H NMR (600 MHz, CD$_3$OD) δ: 9.65-9.76 (m, 1H), 9.02-9.13 (m, 1H), 8.25-8.35 (m, 1H), 7.98-8.07 (m, 1H), 7.72-7.81 (m, 1H), 7.53-7.64 (m, 2H), 7.37-7.49 (m, 3H), 6.73 (s, 1H), 4.88-4.92 (m, 2H), 4.17 (d, J = 9.39 Hz, 4H), 3.39-3.47 (m, 1H), 3.22-3.30 (m, 2H), 1.54 (d, J = 6.46 Hz, 2H), 1.41-1.50 (m, 2H), 0.89-0.96 (m, 3H) |
| 17 | 1-({4-[5-(2-phenylheptyl)-1,3,4-oxadiazol-2-yl]naphthalen-1-yl}methyl)azetidine-3-carboxylic acid | 21 | $^1$H NMR (600 MHz, CD$_3$OD) δ: 8.76 (d, J = 8.22 Hz, 1H), 8.24 (d, J = 8.51 Hz, 1H), 7.90 (d, J = 7.63 Hz, 1H), 7.59-7.72 (m, 3H), 7.28 (d, J = 7.34 Hz, 2H), 7.23-7.26 (m, 2H), 7.18-7.22 (m, 1H), 4.48 (s, 2H), 3.86-3.92 (m, 2H), 3.78-3.82 (m, 2H), 3.32-3.39 (m, 2H), 3.18-3.30 (m, 2H), 1.70-1.90 (m, 2H), 1.14-1.37 (m, 6H), 0.84 (t, J = 6.90 Hz, 3H) |

TABLE 8-continued

| Cmpd No. | Structure IUPAC Name | Starting Interm. | $^1$H NMR δ (ppm) |
|---|---|---|---|
| 18 | 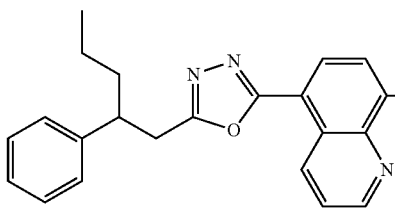<br>1-({5-[5-(2-phenylpentyl)-1,3,4-oxadiazol-2-yl]quinolin-8-yl}methyl)azetidine-3-carboxylic acid | 22 | $^1$H NMR (600 MHz, CD$_3$OD) δ: 9.27-9.39 (m, 1H), 9.00-9.11 (m, 1H), 8.04-8.14 (m, 1H), 7.92-8.02 (m, 1H), 7.66-7.77 (m, 1H), 7.24-7.32 (m, 4H), 7.20 (s, 1H), 4.13 (t, J = 8.22 Hz, 4H), 3.37-3.45 (m, 2H), 3.31 (td, J = 1.61, 3.23 Hz, 3H), 3.22-3.29 (m, 1H), 1.73-1.92 (m, 2H), 1.16-1.36 (m, 2H), 0.91 (t, J = 7.19 Hz, 3H) |
| 23 | 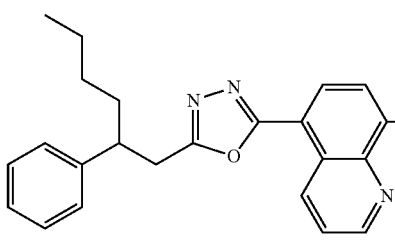<br>1-({5-[5-(2-phenylhexyl)-1,3,4-oxadiazol-2-yl]quinolin-8-yl}methyl)azetidine-3-carboxylic acid | 25 | $^1$H NMR (600 MHz, CD$_3$OD) δ 9.35 (dd, J = 1.61, 8.66 Hz, 1H), 9.05 (dd, J = 1.47, 4.11 Hz, 1H), 8.07 (d, J = 7.34 Hz, 1H), 7.98 (d, J = 7.34 Hz, 1H), 7.70 (dd, J = 4.25, 8.66 Hz, 1H), 7.24-7.31 (m, 4H), 7.19-7.23 (m, 1H), 4.91 (s, 2H), 4.18 (d, J = 8.80 Hz, 4H), 3.37-3.47 (m, 2H), 3.28-3.34 (m, 1H), 3.19-3.27 (m, 1H), 1.75-1.94 (m, 2H), 1.14-1.42 (m, 4H), 0.86 (t, J = 7.19 Hz, 3H) |
| 24 | 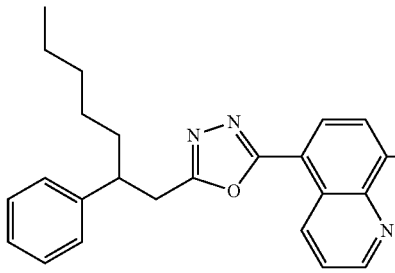<br>1-({5-[5-(2-phenylheptyl)-1,3,4-oxadiazol-2-yl]quinolin-8-yl}methyl)azetidine-3-carboxylic acid | 26 | $^1$H NMR (600 MHz, CD$_3$OD) δ 9.33 (dd, J = 1.47, 8.51 Hz, 1H), 9.03 (dd, J = 1.47, 4.11 Hz, 1H), 8.06 (d, J = 7.63 Hz, 1H), 7.96 (d, J = 7.34 Hz, 1H), 7.68 (dd, J = 4.26, 8.66 Hz, 1H), 7.24-7.32 (m, 4H), 7.19-7.23 (m, 1H), 4.87 (s, 2H), 4.15 (dd, J = 6.02, 8.36 Hz, 4H), 3.37-3.46 (m, 2H), 3.29-3.33 (m, 1H), 3.19-3.26 (m, 1H), 1.75-1.91 (m, 2H), 1.15-1.42 (m, 6H), 0.84 (t, J = 7.04 Hz, 3H) |

Example 10

Biological Data

Compounds were synthesized and tested for S1P1 activity using the GTP γ$^{35}$S binding assay. These compounds may be assessed for their ability to activate or block activation of the human S1P1 receptor in cells stably expressing the S1P1 receptor.

GTP γ$^{35}$S binding was measured in medium containing (mM) HEPES 25, pH 7.4, MgCl$_2$ 10, NaCl 100, dithiothreitol 0.5, digitonin 0.003%, 0.2 nM GTP γ$^{35}$S, and 5 microgram membrane protein in a volume of 150 microliters. Test compounds were included in the concentration range from 0.08 to 5,000 nM unless indicated otherwise. Membranes were incubated with 100 μM 5'-adenylylimmidodiphosphate for 30 min, and subsequently with 10 micromolar GDP for 10 min on ice. Drug solutions and membrane were mixed, and then reactions were initiated by adding GTP γ$^{35}$S and continued for 30 min at 25° C. Reaction mixtures were filtered over Whatman GF/B filters under vacuum, and washed three times with 3 mL of ice-cold buffer (HEPES 25, pH7.4, MgCl$_2$ 10 and NaCl 100). Filters were dried and mixed with scintillant, and counted for $^{35}$S activity using a β-counter. Agonist-induced GTP γ$^{35}$S binding was obtained by subtracting that in the absence of agonist. Binding data were analyzed using a non-linear regression method. In case of antagonist assay, the reaction mixture contained 10 nM S1P1 in the presence of test antagonist at concentrations ranging from 0.08 to 5000 nM. Table 9 shows activity potency: S1P1 receptor from GTP γ³⁵S: nM (EC$_{50}$).

TABLE 9

| Cmpd No. | IUPAC name | S1P1 EC$_{50}$ (nM) |
|---|---|---|
| 1 | (3-{[(4-{5-[(1E)-2-phenylpent-1-en-1-yl]-1,3,4-oxadiazol-2-yl}naphthalen-1-yl)methyl]amino}propyl)phosphonic acid | 27 |
| 2 | 3-{[(4-{5-[(1E)-2-phenylpent-1-en-1-yl]-1,3,4-oxadiazol-2-yl}naphthalen-1-yl)methyl]amino}propanoic acid | 571 |
| 3 | (3-{[(4-{5-[(1E)-2-phenylhex-1-en-1-yl]-1,3,4-oxadiazol-2-yl}naphthalen-1-yl)methyl]amino}propyl) phosphonic acid | 2.52 |
| 4 | 3-{[(4-{5-[(1E)-2-phenylhex-1-en-1-yl]-1,3,4-oxadiazol-2-yl}naphthalen-1-yl)methyl]amino}propanoic acid | 85 |
| 5 | (3-{[(5-{5-[(1E)-2-phenylpent-1-en-1-yl]-1,3,4-oxadiazol-2-yl}quinolin-8-yl)methyl]amino}propyl) phosphonic acid | 0.61 |
| 6 | 3-{[(5-{5-[(1E)-2-phenylpent-1-en-1-yl]-1,3,4-oxadiazol-2-yl}quinolin-8-yl)methyl]amino}propanoic acid | 150 |
| 7 | (3-{[(5-{5-[(1E)-2-phenylhex-1-en-1-yl]-1,3,4-oxadiazol-2-yl}quinolin-8-yl)methyl]amino}propyl) phosphonic acid | 0.5 |
| 8 | 3-{[(5-{5-[(1E)-2-phenylhex-1-en-1-yl]-1,3,4-oxadiazol-2-yl}quinolin-8-yl)methyl]amino}propanoic acid | 33 |
| 9 | {3-[({4-[5-(2-phenylheptyl)-1,3,4-oxadiazol-2-yl]naphthalen-1-yl}methyl)amino]propyl}phosphonic acid | 14 |
| 10 | 3-[({4-[5-(2-phenylheptyl)-1,3,4-oxadiazol-2-yl]naphthalen-1-yl}methyl)amino]propanoic acid | 320 |
| 11 | {3-[({5-[5-(2-phenylpentyl)-1,3,4-oxadiazol-2-yl]quinolin-8-yl}methyl)amino]propyl}phosphonic acid | 0.26 |
| 12 | 3-[({5-[5-(2-phenylpentyl)-1,3,4-oxadiazol-2-yl]quinolin-8-yl}methyl)amino]propanoic acid | 340 |
| 13 | 1-[(4-{5-[(1E)-2-phenylpent-1-en-1-yl]-1,3,4-oxadiazol-2-yl}naphthalen-1-yl)methyl]azetidine-3-carboxylic acid | 607 |
| 14 | 1-[(4-{5-[(1E)-2-phenylhex-1-en-1-yl]-1,3,4-oxadiazol-2-yl}naphthalen-1-yl)methyl]azetidine-3-carboxylic acid | 156 |
| 15 | (E)-1-((5-(5-(2-phenylpent-1-en-1-yl)-1,3,4-oxadiazol-2-yl)quinolin-8-yl)methyl)azetidine-3-carboxylic acid | 163 |
| 16 | 1-[(5-{5-[(1E)-2-phenylhex-1-en-1-yl]-1,3,4-oxadiazol-2-yl}quinolin-8-yl)methyl]azetidine-3-carboxylic acid | 29 |
| 17 | 1-({4-[5-(2-phenylheptyl)-1,3,4-oxadiazol-2-yl]naphthalen-1-yl}methyl)azetidine-3-carboxylic acid | 942 |
| 18 | 1-({5-[5-(2-phenylpentyl)-1,3,4-oxadiazol-2-yl]quinolin-8-yl}methyl)azetidine-3-carboxylic acid | 461 |
| 19 | 3-[({5-[5-(2-phenylhexyl)-1,3,4-oxadiazol-2-yl]quinolin-8-yl}methyl)amino]propanoic acid | 257 |
| 20 | 3-[({5-[5-(2-phenylheptyl)-1,3,4-oxadiazol-2-yl]quinolin-8-yl}methyl)amino]propanoic acid | 417 |
| 21 | {3-[({5-[5-(2-phenylhexyl)-1,3,4-oxadiazol-2-yl]quinolin-8-yl}methyl)amino]propyl}phosphonic acid | 1.05 |
| 22 | {3-[({5-[5-(2-phenylheptyl)-1,3,4-oxadiazol-2-yl]quinolin-8-yl}methyl)amino]propyl}phosphonic acid | 2.87 |
| 23 | 1-({5-[5-(2-phenylhexyl)-1,3,4-oxadiazol-2-yl]quinolin-8-yl}methyl)azetidine-3-carboxylic acid | 376 |
| 24 | 1-({5-[5-(2-phenylheptyl)-1,3,4-oxadiazol-2-yl]quinolin-8-yl}methyl)azetidine-3-carboxylic acid | 1091 |

What is claimed is:

1. A compound of Formula I:

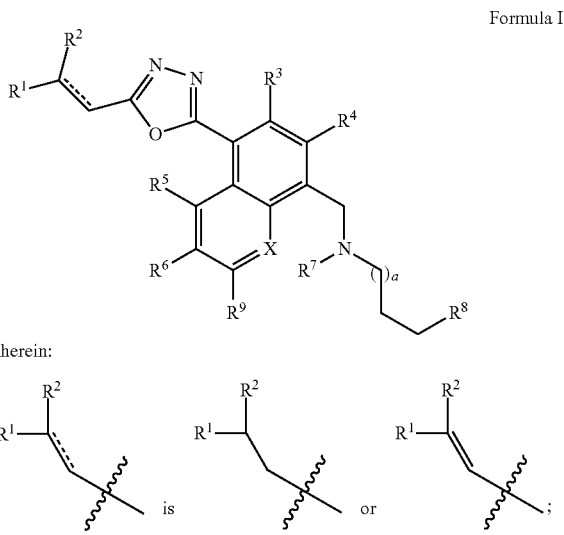

Formula I wherein:

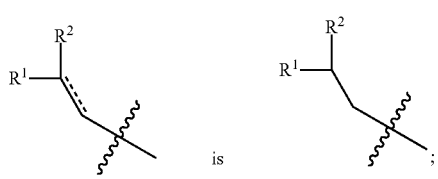

X is N or CR$^{12}$;

R$^1$ is substituted or unsubstituted aryl, substituted or unsubstituted heterocycle, substituted or unsubstituted C$_{5-8}$ cycloalkyl, or substituted or unsubstituted C$_{5-8}$ cycloalkenyl;

R$^2$ is substituted or unsubstituted C$_{1-8}$ alkyl;

R$^3$ is hydrogen, halogen, substituted or unsubstituted C$_{1-8}$ alkyl, C(O)R$^{13}$ or hydroxyl;

R$^4$ is hydrogen, halogen, substituted or unsubstituted C$_{1-8}$ alkyl, C(O)R$^{13}$ or hydroxyl;

R$^5$ is hydrogen, halogen, substituted or unsubstituted C$_{1-8}$ alkyl, C(O)R$^{13}$, hydroxyl or substituted or unsubstituted heterocycle;

R$^6$ is hydrogen, halogen, substituted or unsubstituted C$_{1-8}$ alkyl, C(O)R$^{13}$, hydroxyl or substituted or unsubstituted heterocycle;

R$^7$ is hydrogen or substituted or unsubstituted C$_{1-8}$ alkyl;

R$^8$ is —OPO$_3$H$_2$, carboxylic acid, —PO$_3$H$_2$, —P(O)MeOH, —P(O)(H)OH or OR$^{10}$;

R$^9$ is hydrogen, halogen, substituted or unsubstituted C$_{1-8}$ alkyl, C(O)R$^{13}$, hydroxyl or substituted or unsubstituted heterocycle;

R$^{10}$ is hydrogen or substituted or unsubstituted C$_{1-8}$ alkyl;

R$^{12}$ is hydrogen, halogen, substituted or unsubstituted C$_{1-8}$ alkyl, C(O)R$^{13}$ or hydroxyl;

R$^{13}$ is OH, substituted or unsubstituted C$_{1-8}$ alkyl or —OC$_{1-8}$ alkyl; and a is 0, 1, 2 or 3;

or an enantiomer or diastereoisomer thereof, or a tautomer or zwitterion of any one of the foregoing, or a pharmaceutically acceptable salt of any one of the foregoing.

2. A compound according to claim 1, wherein a is 0 or 1.

3. A compound according to claim 2, wherein:

R[1] is substituted or unsubstituted aryl;
R[2] is substituted or unsubstituted $C_{1-8}$ alkyl;
R[3] is hydrogen;
R[4] is hydrogen;
R[5] is hydrogen;
R[6] is hydrogen;
R[7] is hydrogen;
R[8] is carboxylic acid or —$PO_3H_2$;
R[9] is hydrogen; and
R[12] is hydrogen.

4. A compound according to claim 3, wherein:
R[1] unsubstituted aryl; and
R[2] is unsubstituted $C_{1-8}$ alkyl.

5. A compound according to claim 2, wherein:

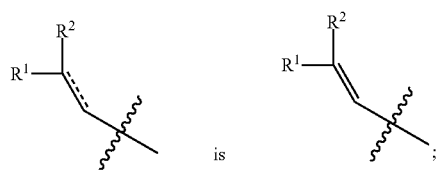

is

R[1] is substituted or unsubstituted aryl;
R[2] is substituted or unsubstituted $C_{1-8}$ alkyl;
R[3] is hydrogen;
R[4] is hydrogen;
R[5] is hydrogen;
R[6] is hydrogen;
R[7] is hydrogen;
R[8] is carboxylic acid or —$PO_3H_2$; and
R[9] is hydrogen.

6. A compound according to claim 5, wherein:
R[1] unsubstituted aryl; and
R[2] is unsubstituted $C_{1-8}$ alkyl.

7. A compound according to claim 1 selected from:

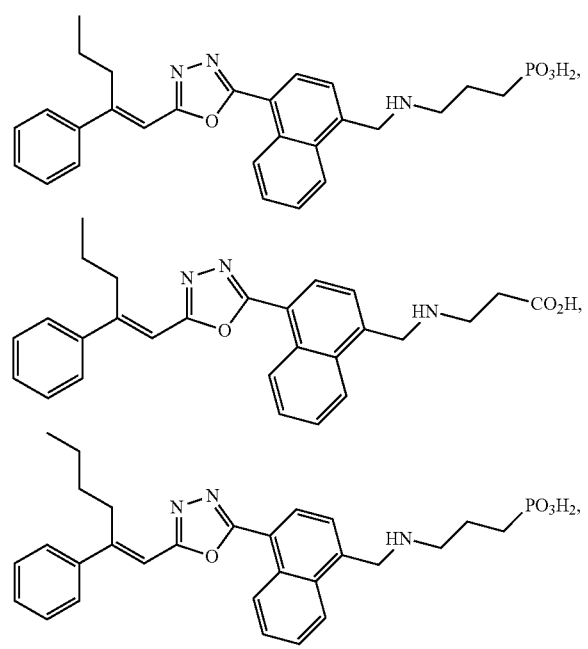

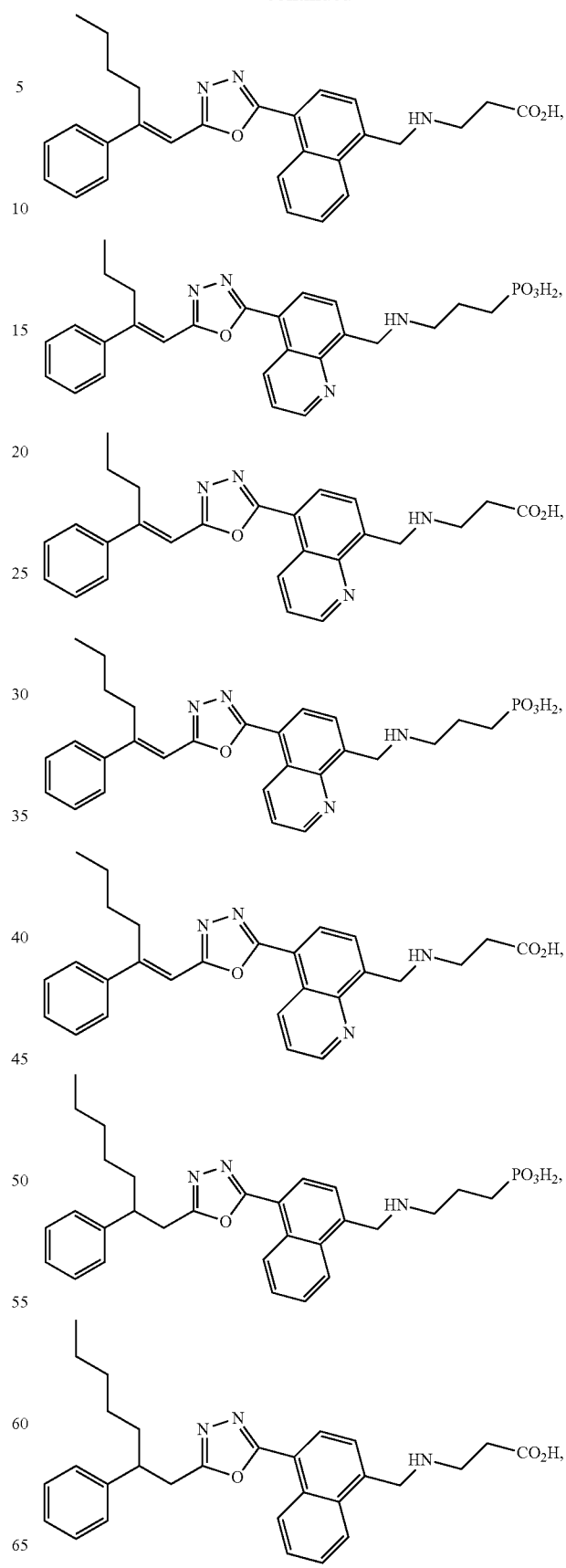

-continued

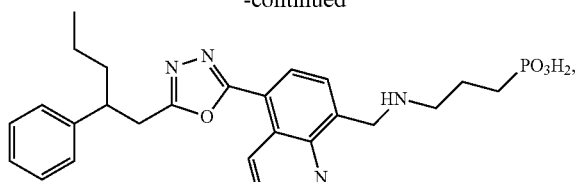

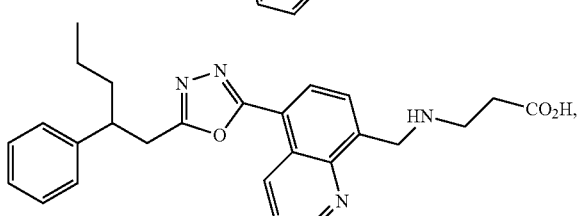

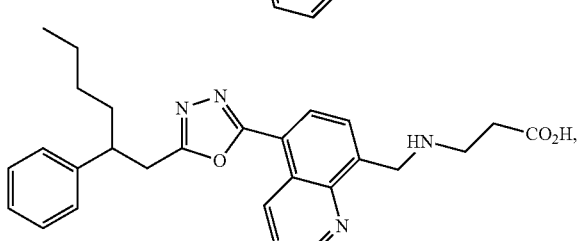

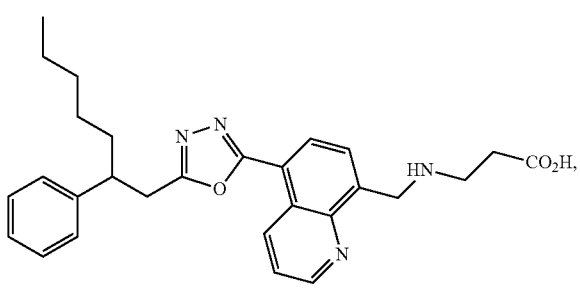

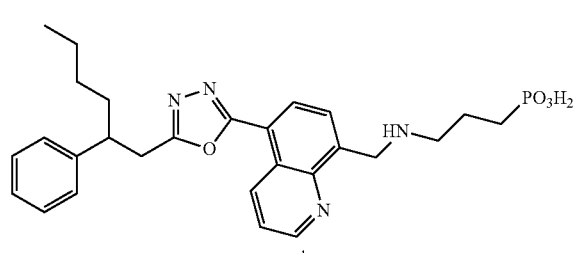

and

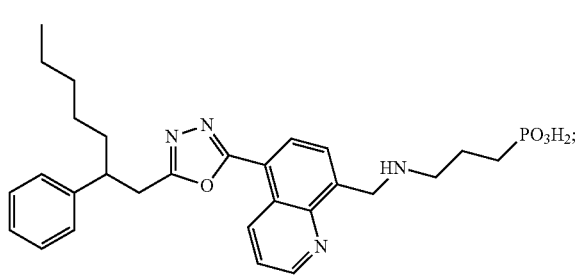

and pharmaceutically acceptable salts thereof.

8. A pharmaceutical composition comprising as active ingredient a therapeutically effective amount of a compound of claim 1 and a pharmaceutically acceptable adjuvant, diluent or carrier.

9. A compound of Formula II:

Formula II

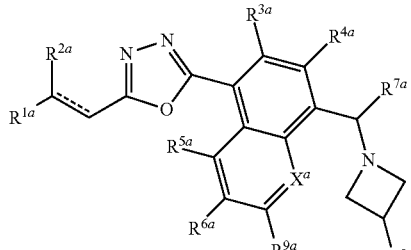

wherein:

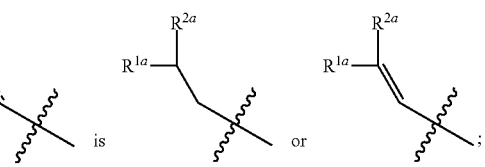

$X^a$ is N or $CR^{12a}$;
$R^{1a}$ is substituted or unsubstituted aryl, substituted or unsubstituted heterocycle, substituted or unsubstituted $C_{5-8}$ cycloalkyl, or substituted or unsubstituted $C_{5-8}$ cycloalkenyl;
$R^{2a}$ is substituted or unsubstituted $C_{1-8}$ alkyl;
$R^{3a}$ is hydrogen, halogen, substituted or unsubstituted $C_{1-8}$ alkyl, $C(O)R^{13a}$ or hydroxyl;
$R^{4a}$ is hydrogen, halogen, substituted or unsubstituted $C_{1-8}$ alkyl, $C(O)R^{13a}$ or hydroxyl;
$R^{5a}$ is hydrogen, halogen, substituted or unsubstituted $C_{1-8}$ alkyl, $C(O)R^{13a}$, hydroxyl or substituted or unsubstituted heterocycle;
$R^{6a}$ is hydrogen, halogen, substituted or unsubstituted $C_{1-8}$ alkyl, $C(O)R^{13a}$, hydroxyl or substituted or unsubstituted heterocycle;
$R^{7a}$ is hydrogen or substituted or unsubstituted $C_{1-8}$ alkyl;
$R^{8a}$ is $-OPO_3H_2$, carboxylic acid, $-PO_3H_2$, $-P(O)MeOH$, $-P(O)(H)OH$ or $OR^{10a}$;
$R^{9a}$ is hydrogen, halogen, substituted or unsubstituted $C_{1-8}$ alkyl, $C(O)R^{13a}$, hydroxyl or substituted or unsubstituted heterocycle;
$R^{10a}$ is hydrogen or substituted or unsubstituted $C_{1-8}$ alkyl;
$R^{12a}$ is hydrogen, halogen, substituted or unsubstituted $C_{1-8}$ alkyl, $C(O)R^{13a}$ or hydroxyl; and
$R^{13a}$ is hydroxyl, substituted or unsubstituted $C_{1-8}$ alkyl or $-OC_{1-8}$ alkyl;

or an enantiomer or diastereoisomer thereof, or a tautomer or zwitterion of any one of the foregoing, or a pharmaceutically acceptable salt of any one of the foregoing.

10. A compound according to claim 9, wherein:

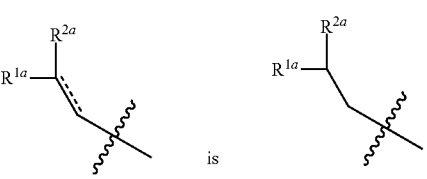

$R^{1a}$ is substituted or unsubstituted aryl;
$R^{2a}$ is substituted or unsubstituted $C_{1-8}$ alkyl;
$R^{3a}$ is hydrogen;
$R^{4a}$ is hydrogen;

$R^{5a}$ is hydrogen;
$R^{6a}$ is hydrogen;
$R^{7a}$ is hydrogen;
$R^{8a}$ is carboxylic acid; and
$R^{9a}$ is hydrogen.

11. A compound according to claim 10, wherein:
$R^{1a}$ is unsubstituted aryl; and
$R^{2a}$ is unsubstituted $C_{1-8}$ alkyl.

12. A compound according to claim 9, wherein:

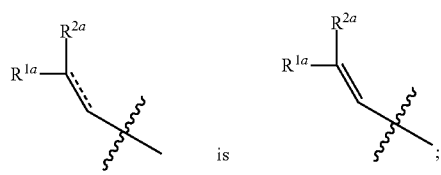

$R^{1a}$ is substituted or unsubstituted aryl;
$R^{2a}$ is substituted or unsubstituted $C_{1-8}$ alkyl;
$R^{3a}$ is hydrogen;
$R^{4a}$ is hydrogen;
$R^{5a}$ is hydrogen;
$R^{6a}$ is hydrogen;
$R^{7a}$ is hydrogen;
$R^{8a}$ is carboxylic acid; and
$R^{9a}$ is hydrogen.

13. A compound according to claim 12, wherein:
$R^{1a}$ is unsubstituted aryl; and
$R^{2a}$ is unsubstituted $C_{1-8}$ alkyl.

14. A compound according to claim 9 selected from:

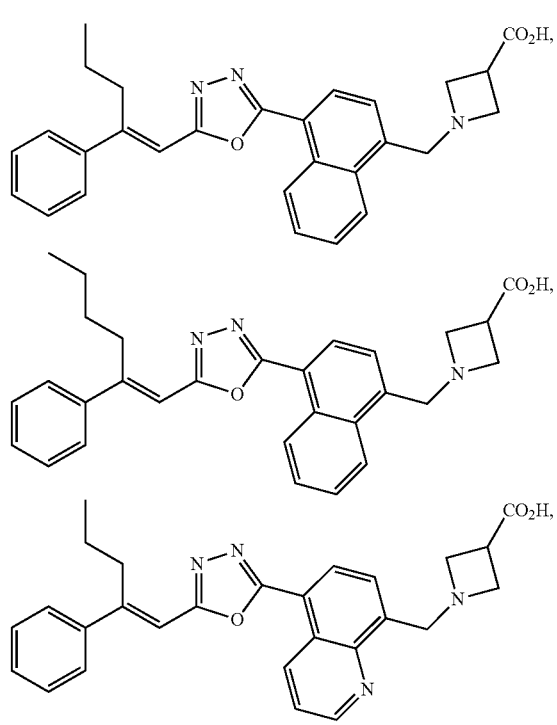

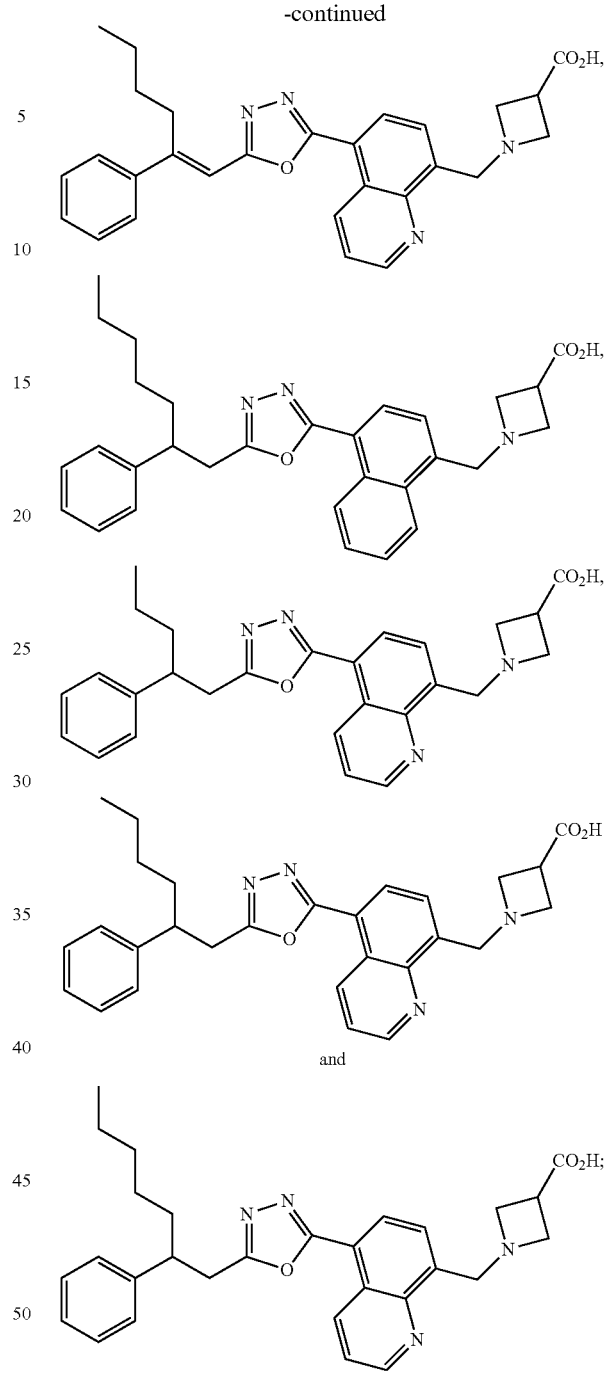

and pharmaceutically acceptable salts thereof.

15. A pharmaceutical composition comprising as active ingredient a therapeutically effective amount of a compound of claim 9 and a pharmaceutically acceptable adjuvant, diluent or carrier.

16. A method of treating an autoimmune disease in a subject, the method comprising administering to the subject a therapeutically effective amount of a compound of claim 1 or a pharmaceutically acceptable salt thereof, thereby treating the disease in the subject.

17. The method of claim 16, wherein the disease is systemic lupus erythematosus or inflammatory bowel disease.

18. A method of treating an autoimmune disease in a subject, the method comprising administering to the subject a therapeutically effective amount of a compound of claim 9 or a pharmaceutically acceptable salt thereof, thereby treating the disease in the subject.

19. The method of claim 18, wherein the disease or condition is systemic lupus erythematosus or inflammatory bowel disease.

* * * * *